United States Patent
Lalli et al.

(10) Patent No.: US 11,896,201 B2
(45) Date of Patent: Feb. 13, 2024

(54) INSERTABLE SLEEVE FOR SPECULUM AND USE THEREOF

(71) Applicant: CEEK Women's Health, Inc., Portland, OR (US)

(72) Inventors: Maria Lalli, Portland, OR (US); Fahti Self, Portland, OR (US); Darius Naigamwalla, Portland, OR (US)

(73) Assignee: CEEK WOMEN'S HEALTH, INC., Portland, OR (US)

( * ) Notice: Subject to any disclaimer, the term of this patent is extended or adjusted under 35 U.S.C. 154(b) by 32 days.

(21) Appl. No.: 17/315,072

(22) Filed: May 7, 2021

(65) Prior Publication Data

US 2022/0095898 A1 Mar. 31, 2022

Related U.S. Application Data

(63) Continuation of application No. 15/393,081, filed on Dec. 28, 2016, now abandoned.

(60) Provisional application No. 62/310,604, filed on Mar. 18, 2016, provisional application No. 62/281,694, filed on Jan. 21, 2016, provisional application No. 62/272,619, filed on Dec. 29, 2015.

(51) Int. Cl.
*A61B 1/00* (2006.01)
*A61B 1/32* (2006.01)
*A61B 1/303* (2006.01)

(52) U.S. Cl.
CPC ...... *A61B 1/00142* (2013.01); *A61B 1/00135* (2013.01); *A61B 1/00154* (2013.01); *A61B 1/303* (2013.01); *A61B 1/32* (2013.01)

(58) Field of Classification Search
CPC . A61B 1/00135; A61B 1/00103; A61B 1/303; A61B 1/32; A61B 90/04; A61F 6/18
USPC .................................................. 600/201–245
See application file for complete search history.

(56) References Cited

U.S. PATENT DOCUMENTS

| | | |
|---|---|---|
| 55,511 A | 6/1866 | Lentz |
| 977,489 A | 12/1910 | Unruh |
| 1,969,671 A | 8/1934 | Archer |
| 2,083,573 A | 6/1937 | Morgan |
| 2,123,343 A | 7/1938 | Rightsell |
| 2,324,485 A | 7/1943 | Chamberlain, Jr. |
| 2,509,241 A | 5/1950 | Mende |
| 2,579,849 A | 12/1951 | Newman |

(Continued)

FOREIGN PATENT DOCUMENTS

| CN | 201595813 U | 10/2010 |
|---|---|---|
| CN | 201996970 U | 10/2011 |

(Continued)

*Primary Examiner* — Eduardo C Robert
*Assistant Examiner* — Tara Rose E Carter
(74) *Attorney, Agent, or Firm* — Mintz, Levin, Cohn, Ferris, Glovsky and Popeo, P.C.

(57) ABSTRACT

An insertable sleeve accessory and a method for use is provided. The insertable sleeve includes a cylindrical sleeve body. The cylindrical sleeve body includes an outer surface and an inner surface, the inner surface defining a hollow sleeve channel, and at least one open end. The cylindrical sleeve body is configured to be inserted into a vaginal cavity of a patient. The sleeve body is further configured to receive an insertion portion of a medical speculum in the hollow sleeve channel subsequent to being inserted into the vaginal cavity.

20 Claims, 17 Drawing Sheets

(56) References Cited

U.S. PATENT DOCUMENTS

| | | |
|---|---|---|
| 2,670,736 A | 3/1954 | Dunkelberger |
| 2,714,886 A | 8/1955 | Charles |
| 2,884,925 A | 5/1959 | Meynier, Jr. |
| 2,954,025 A | 9/1960 | Grieshaber |
| 3,110,305 A | 11/1963 | Sygnator |
| 3,139,886 A | 7/1964 | Tallman et al. |
| 3,246,646 A | 4/1966 | Murphy, Jr. |
| 3,324,850 A | 6/1967 | Emmett et al. |
| 3,332,414 A | 7/1967 | Gasper |
| 3,532,088 A | 10/1970 | Fiore |
| 3,565,061 A | 2/1971 | Reynolds |
| 3,650,266 A | 3/1972 | Pestka et al. |
| 3,744,481 A | 7/1973 | Mcdonald |
| 3,752,149 A | 8/1973 | Rosenthal et al. |
| 3,762,400 A | 10/1973 | Mc |
| 3,769,968 A | 11/1973 | Blount et al. |
| 3,815,585 A | 6/1974 | Fiore |
| 3,841,317 A | 10/1974 | Awais |
| 3,851,642 A | 12/1974 | Mcdonald |
| 3,857,395 A | 12/1974 | Johnson et al. |
| 3,885,563 A | 5/1975 | Johnson et al. |
| 3,890,961 A | 6/1975 | Moore et al. |
| 4,004,591 A | 1/1977 | Freimark |
| 4,010,751 A | 3/1977 | Ring |
| 4,344,419 A | 8/1982 | Burgin |
| 4,356,817 A | 11/1982 | Mckibben et al. |
| 4,428,370 A | 1/1984 | Keely |
| 4,492,220 A | 1/1985 | Hayes |
| 4,502,468 A | 3/1985 | Burgin |
| 4,566,439 A | 1/1986 | Burgin |
| 4,597,382 A | 7/1986 | Perez, Jr. |
| 4,638,792 A | 1/1987 | Burgin |
| 4,676,773 A | 6/1987 | Sheldon |
| 4,735,621 A | 4/1988 | Hessel |
| D299,532 S | 1/1989 | Cecil et al. |
| 4,805,604 A | 2/1989 | Spery |
| 4,807,600 A | 2/1989 | Hayes |
| 4,834,077 A | 5/1989 | Sun |
| 4,857,175 A | 8/1989 | Spinnler |
| 4,867,176 A | 9/1989 | Lash |
| 4,945,923 A | 8/1990 | Evans et al. |
| 4,976,273 A | 12/1990 | Hessel |
| 4,981,147 A | 1/1991 | Barnett |
| 4,984,564 A | 1/1991 | Yuen |
| 4,993,433 A | 2/1991 | Reddy |
| 5,007,409 A | 4/1991 | Pope |
| 5,041,080 A | 8/1991 | Shimatani et al. |
| 5,072,720 A | 12/1991 | Francis et al. |
| 5,083,414 A | 1/1992 | Wu |
| 5,094,250 A | 3/1992 | Hessel |
| 5,135,475 A | 8/1992 | Nakanishi et al. |
| 5,156,165 A | 10/1992 | Wu |
| 5,174,278 A | 12/1992 | Babkow |
| 5,179,936 A | 1/1993 | Ohara et al. |
| 5,179,937 A | 1/1993 | Lee |
| 5,193,555 A | 3/1993 | Richardson et al. |
| 5,209,241 A | 5/1993 | Hardy |
| 5,243,966 A | 9/1993 | Ng |
| 5,342,385 A | 8/1994 | Norelli et al. |
| 5,347,995 A | 9/1994 | Slater et al. |
| 5,377,667 A | 1/1995 | Patton et al. |
| 5,433,219 A | 7/1995 | Spery |
| 5,460,165 A | 10/1995 | Mayes |
| 5,505,690 A | 4/1996 | Patton et al. |
| 5,540,658 A | 7/1996 | Evans et al. |
| 5,598,852 A | 2/1997 | Spery |
| 5,622,185 A | 4/1997 | Richardson et al. |
| 5,623,946 A | 4/1997 | Hessel |
| 5,687,741 A | 11/1997 | Torger |
| 5,716,329 A | 2/1998 | Dieter |
| 5,743,852 A | 4/1998 | Johnson |
| 5,785,648 A | 7/1998 | Min |
| 5,865,729 A | 2/1999 | Meehan et al. |
| 5,868,668 A | 2/1999 | Weiss |
| 5,992,415 A | 11/1999 | Alla et al. |
| 6,019,743 A | 2/2000 | Cole et al. |
| 6,024,696 A | 2/2000 | Hoftman et al. |
| 6,036,638 A | 3/2000 | Nwawka |
| 6,048,308 A | 4/2000 | Strong |
| 6,095,998 A | 8/2000 | Osborn et al. |
| 6,096,046 A | 8/2000 | Weiss |
| 6,174,282 B1 | 1/2001 | Tan |
| 6,186,973 B1 | 2/2001 | Buzot |
| 6,248,089 B1 | 6/2001 | Porat |
| 6,254,566 B1 | 7/2001 | Buck et al. |
| 6,280,379 B1 | 8/2001 | Resnick |
| 6,287,251 B1 | 9/2001 | Tan |
| 6,302,862 B1 | 10/2001 | Osborn et al. |
| 6,341,607 B1 | 1/2002 | Couvreur |
| 6,347,243 B1 | 2/2002 | Fraden |
| 6,354,995 B1 | 3/2002 | Hoftman et al. |
| 6,361,543 B1 | 3/2002 | Chin et al. |
| 6,379,299 B1 | 4/2002 | Borodulin et al. |
| 6,395,012 B1 | 5/2002 | Yoon et al. |
| 6,416,466 B1 | 7/2002 | Hsiao |
| 6,416,467 B1 | 7/2002 | Mcmillin et al. |
| 6,428,474 B1 | 8/2002 | Weiss |
| 6,432,048 B1 | 8/2002 | Francois |
| 6,436,033 B2 | 8/2002 | Tan |
| 6,508,780 B1 | 1/2003 | Edgett et al. |
| D474,275 S | 5/2003 | Tan |
| 6,569,091 B2 | 5/2003 | Diokno et al. |
| 6,669,654 B2 | 12/2003 | Diokno et al. |
| 6,702,740 B2 | 3/2004 | Herold |
| 6,902,530 B1 | 6/2005 | Pianka |
| 6,939,289 B2 | 9/2005 | Zunker et al. |
| 7,047,975 B2 | 5/2006 | Austin et al. |
| 7,063,664 B2 | 6/2006 | Mohajer |
| 7,105,007 B2 | 9/2006 | Hibler |
| 7,172,573 B1 | 2/2007 | Lamb |
| 7,311,663 B2 | 12/2007 | Marcotte |
| D558,871 S | 1/2008 | Osterberg |
| 7,322,358 B2 | 1/2008 | Tam et al. |
| 7,338,462 B2 | 3/2008 | Minoguchi et al. |
| 7,371,212 B2 | 5/2008 | Klaassen |
| 7,392,807 B2 | 7/2008 | Osterberg |
| D593,195 S | 5/2009 | Osterberg |
| 7,654,953 B2 | 2/2010 | Borodulin et al. |
| 7,658,712 B2 | 2/2010 | Klaassen et al. |
| 7,665,893 B2 | 2/2010 | Buchalter |
| 7,798,986 B2 | 9/2010 | Melvin et al. |
| 7,810,500 B2 | 10/2010 | Osterberg |
| 7,815,594 B2 | 10/2010 | Dougherty et al. |
| 7,896,806 B2 | 3/2011 | Shah et al. |
| 7,918,004 B2 | 4/2011 | Melvin et al. |
| 8,062,245 B2 | 11/2011 | Gann et al. |
| 8,075,512 B2 | 12/2011 | Sargent et al. |
| 8,083,673 B2 | 12/2011 | Rosen |
| 8,142,352 B2 | 3/2012 | Vivenzio et al. |
| 8,162,872 B2 | 4/2012 | Loyd et al. |
| 8,256,423 B2 | 9/2012 | Osterberg |
| 8,267,860 B2 | 9/2012 | Klaassen et al. |
| D671,642 S | 11/2012 | Grisby |
| 8,435,205 B2 | 5/2013 | Arora et al. |
| 8,449,491 B2 | 5/2013 | Hasse et al. |
| 8,449,492 B2 | 5/2013 | Sargent et al. |
| 8,460,187 B2 | 6/2013 | Bouquet |
| 8,485,196 B2 | 7/2013 | Osterberg |
| 8,539,660 B2 | 9/2013 | Melvin et al. |
| 8,652,035 B2 | 2/2014 | Steigerwald |
| 8,734,414 B2 | 5/2014 | Winkel et al. |
| 8,747,308 B2 | 6/2014 | Muzzammel |
| D710,500 S | 8/2014 | Roeloffs |
| 8,834,362 B2 | 9/2014 | Shipp |
| 8,876,711 B2 | 11/2014 | Lin et al. |
| 8,926,547 B2 | 1/2015 | Arora et al. |
| 8,979,751 B2 | 3/2015 | George |
| 8,979,851 B2 | 3/2015 | Fallin et al. |
| 9,132,043 B2 | 9/2015 | Winkel et al. |
| 9,186,282 B2 | 11/2015 | Ito et al. |
| 9,233,029 B2 | 1/2016 | Gann et al. |
| 9,283,122 B2 | 3/2016 | Taniguchi et al. |
| 9,326,671 B2 | 5/2016 | Roeloffs |
| 10,456,016 B2 | 10/2019 | Lalli et al. |

(56) References Cited

U.S. PATENT DOCUMENTS

| | | |
|---|---|---|
| 10,687,699 B2 | 6/2020 | Lalli et al. |
| D924,397 S | 7/2021 | Lalli et al. |
| 11,147,444 B2 | 10/2021 | Vella et al. |
| D935,610 S | 11/2021 | Wang et al. |
| D986,415 S | 5/2023 | Lalli et al. |
| 2001/0056223 A1 | 12/2001 | Thompson |
| 2002/0115910 A1 | 8/2002 | Diokno et al. |
| 2003/0069477 A1 | 4/2003 | Raisman et al. |
| 2003/0105387 A1 | 6/2003 | Frumovitz et al. |
| 2005/0021069 A1 | 1/2005 | Feuer et al. |
| 2005/0021080 A1 | 1/2005 | Feuer et al. |
| 2005/0085699 A1 | 4/2005 | Weiss |
| 2005/0124860 A1 | 6/2005 | Mohajer |
| 2005/0192482 A1 | 9/2005 | Carpenter et al. |
| 2005/0197615 A1 | 9/2005 | Gann et al. |
| 2005/0273044 A1 | 12/2005 | Gann et al. |
| 2005/0277867 A1 | 12/2005 | Minoguchi et al. |
| 2006/0047285 A1 | 3/2006 | Fields |
| 2006/0079924 A1 | 4/2006 | Sanders et al. |
| 2006/0084843 A1 | 4/2006 | Sommerich et al. |
| 2006/0122463 A1 | 6/2006 | Klaassen |
| 2007/0032758 A1 | 2/2007 | Chase et al. |
| 2007/0032814 A1 | 2/2007 | Hibler |
| 2007/0156022 A1 | 7/2007 | Patel |
| 2008/0058605 A1 | 3/2008 | Sorensen |
| 2008/0114210 A1 | 5/2008 | Shah et al. |
| 2008/0242938 A1 | 10/2008 | Larkin |
| 2008/0262407 A1 | 10/2008 | Chase et al. |
| 2008/0287744 A1 | 11/2008 | Borodulin et al. |
| 2008/0306345 A1 | 12/2008 | Balas |
| 2009/0062691 A1 | 3/2009 | Kim |
| 2009/0099422 A1 | 4/2009 | George |
| 2009/0326331 A1 | 12/2009 | Rosen |
| 2011/0009803 A1 | 1/2011 | Dougherty et al. |
| 2011/0040234 A1 | 2/2011 | Chaffringeon |
| 2011/0237902 A1 | 9/2011 | Rosen |
| 2012/0220918 A1 | 8/2012 | Chaffringeon |
| 2013/0197314 A1 | 8/2013 | Eakin |
| 2014/0081281 A1 | 3/2014 | Felder |
| 2014/0109915 A1 | 4/2014 | Reddy et al. |
| 2014/0163322 A1 | 6/2014 | Mehta |
| 2015/0057502 A1 | 2/2015 | George |
| 2015/0112148 A1 | 4/2015 | Bouquet |
| 2015/0290440 A1 | 10/2015 | Redol |
| 2017/0181605 A1 | 6/2017 | Lalli et al. |
| 2017/0181615 A1 | 6/2017 | Vella et al. |
| 2017/0181616 A1 | 6/2017 | Vella et al. |
| 2018/0263480 A1 | 9/2018 | Lalli et al. |
| 2022/0087512 A1 | 3/2022 | Lalli et al. |
| 2022/0104699 A1 | 4/2022 | Self et al. |
| 2022/0175239 A1 | 6/2022 | Vella et al. |

FOREIGN PATENT DOCUMENTS

| | | | |
|---|---|---|---|
| EM | 008460802-0002 A1 | 3/2021 | |
| EM | 008460802-0003 A1 | 3/2021 | |
| EM | 008460802-0004 A1 | 3/2021 | |
| EM | 008460802-0005 A1 | 3/2021 | |
| EM | 008460802-0006 A1 | 3/2021 | |
| EM | 008460802-0007 A1 | 3/2021 | |
| EM | 0084608020001 A1 | 3/2021 | |
| GB | 2424585 A | 10/2006 | |
| GB | 2459076 A | 10/2009 | |
| GB | 6123744 | 3/2021 | |
| GB | 6123745 | 3/2021 | |
| GB | 6123747 | 3/2021 | |
| WO | 9811818 A1 | 3/1998 | |
| WO | WO-9833431 A1 * | 8/1998 | ......... A61B 1/00135 |
| WO | 2009000078 A1 | 12/2008 | |
| WO | 2011024901 A1 | 3/2011 | |
| WO | 2017117308 A2 | 7/2017 | |
| WO | 2017117310 A2 | 7/2017 | |
| WO | 2017117313 A2 | 7/2017 | |
| WO | 2020076967 A1 | 4/2020 | |

* cited by examiner

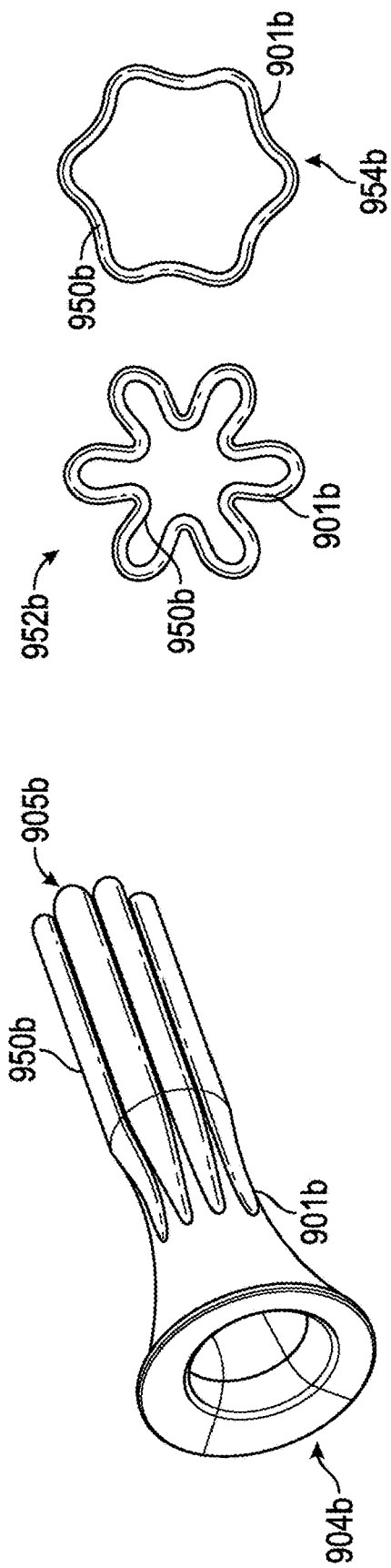
FIG. 8D
FIG. 8E
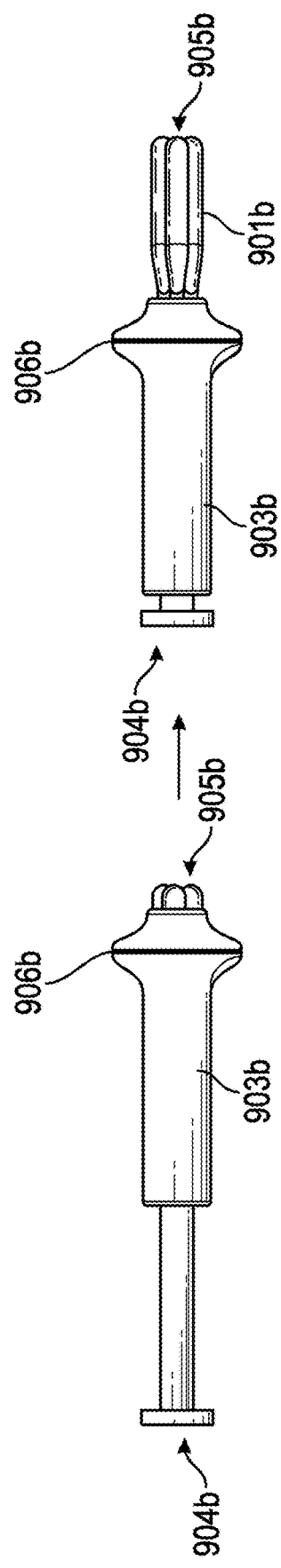
FIG. 8F

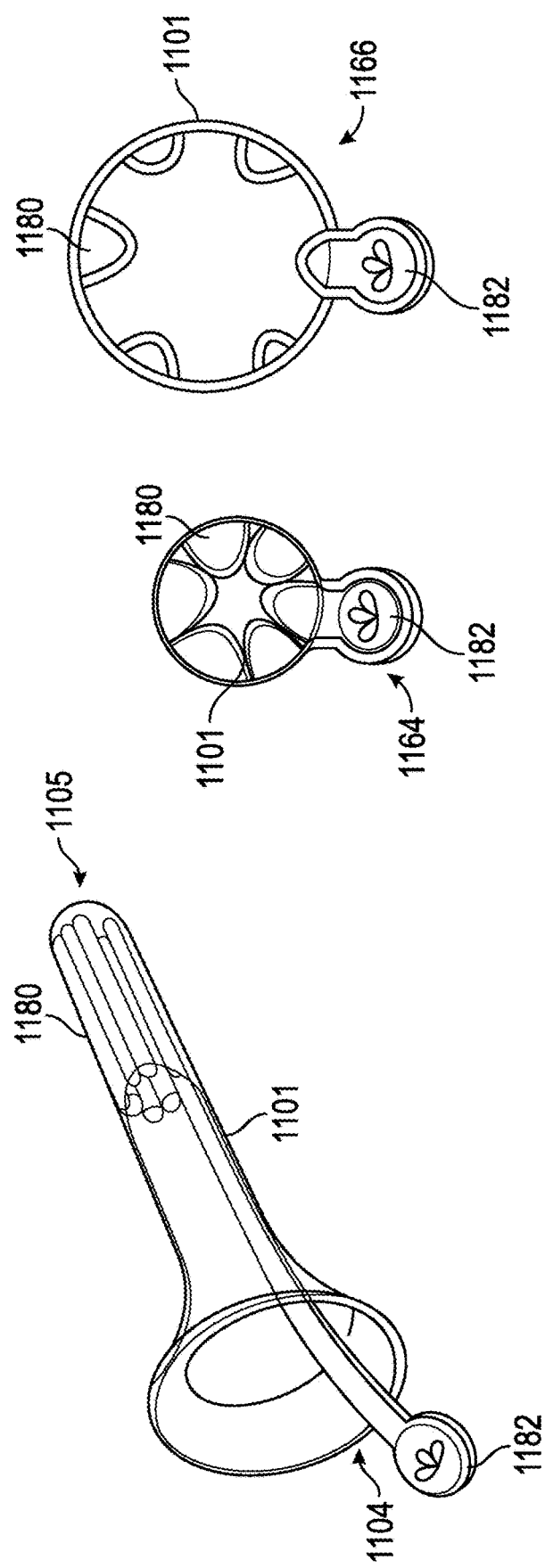
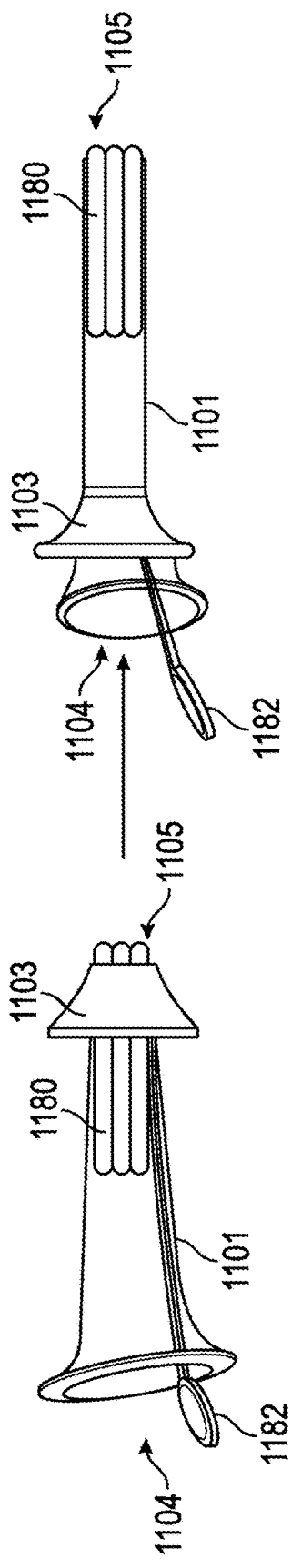
FIG 8K
FIG. 8L
FIG. 8M

INSERTABLE SLEEVE FOR SPECULUM AND USE THEREOF

CROSS-REFERENCE TO RELATED PATENT APPLICATIONS

This application claims the benefit of and priority to U.S. Provisional Patent Application No. 62/272,619 filed Dec. 29, 2015, entitled "Insertable Sleeve for Speculum and Use Thereof," U.S. Provisional Patent Application No. 62/281,694 filed Jan. 21, 2016, entitled "Insertable Sleeve for Speculum and Use Thereof," and U.S. Provisional Patent Application No. 62/310,604 filed Mar. 18, 2016, entitled "Insertable Sleeve for Speculum and Use Thereof." Each of the aforementioned provisional applications is incorporated herein by reference in its entirety.

BACKGROUND

The present invention relates generally to the field of a medical speculum.

A speculum is a medical tool used to provide visualization into a body cavity. Speculums or specula are traditionally used for viewing and accessing the vaginal cavity for gynecology patients. The traditional speculum consists of two blades with a hinge and a handle. The blades are inserted into the body cavity in a closed position, and separated by squeezing two pieces of the handle together or applying force to a lever attached to the handle, thereby dilating the vagina and providing visualization of and accessibility to the vagina, the cervix, and surrounding areas. Once opened, the speculum can be locked in an open position, e.g., by using a screw-based mechanism so an operator (e.g., physician, nurse, mid-wife, etc.) does not need to continue squeezing the pieces of the handle or the lever during the inspection. The operator can then proceed with inspecting the vagina, conducting a Pap smear, or any other medical procedures that may need to be provided.

The double blade design of speculum devices has been in use since the 1800s, and few changes have been made to the original design. The biggest changes with the double blade design have been changes in the material from metal to plastic and the addition of internal lighting on some models of the speculum so that the operator does not have to rely on external lighting to gain a clear view of the vagina and the cervix.

A few, less widely used alternative speculum designs exist. About fifteen years ago, an inflatable speculum was developed, but it failed to gain any traction in the market and was quickly discontinued. The inflatable speculum was inserted into the vagina, and air was used to inflate a tube of the speculum to open the vaginal canal and exert pressure equally on all sides of the canal. However, there were a number of problems with this concept: (1) The tube filled the entire cavity and prevented the operator from seeing the vaginal walls, which can be useful for diagnosing infections or lesions. (2) The inflation technology used to operate the device included an extremely noisy inflatable pump mechanism that increased patient anxiety and discomfort during the examination process (though other traditional speculum designs also employ mechanisms that are noisy to manipulate and actuate, and create patient anxiety during a procedure). Another alternative speculum design includes a stopper that prevents air from leaving the vagina upon insertion of the speculum into the vagina. Air can then be pumped inside the vagina to open the vagina during examination. However, this method relies on cameras for viewing because having a viewing opening between the cervix and the operator would allow the escape of air, deflating the vagina. Additionally, in both cases, the air alone may not have the strength to hold the vagina open as the vaginal walls can exert significant inward force, collapsing the field of view. Moreover, the noises and feeling of the inflation of a device inside the vagina, or air being pushed inside the vagina, may be uncomfortable for patients both physically and emotionally.

Still, there are drawbacks with the traditional two blade design. For one, tissue can enter between the blades once they are opened inside the vaginal cavity, a common occurrence that providers characterize as "side wall encroachment." Women, especially obese women, women with multiple vaginal births, or those with vaginal laxity, may have extra tissue in the side walls of the vagina that may fall into the space between the two blades once opened. This can cause problems for operators, particularly in providing clear visualization of the vagina and cervix, which potentially limits the effectiveness of the procedure. Furthermore, with all patients, when trying to close the speculum blades, tissue and/or pubic hair may become pinched between the blades. Pinching is extremely painful for patients and difficult for the operator to avoid without removing the speculum in an open position, which causes significant discomfort to the patients as well. There are no satisfactory solutions for these problems, resulting in tremendous patient discomfort with the entire speculum experience.

In an attempt to limit sidewall encroachment and allow for better visualization of the vaginal walls and cervix, operators may attempt to place condoms or portions of medical gloves over the speculum. This is an unsatisfactory and ineffective approach as condoms and gloves were not designed to support the internal pressure of the vaginal walls, but to be as thin as possible. Furthermore, using these solutions can result in both condoms and glove fingers, or torn portions of them, being left behind in the vaginal cavity following removal of the speculum. Alternatively, operators may choose to use larger speculums to provide a larger viewing/accessing window to compensate for tissue entering the side of the speculum between the blades. However, increasing the size of the speculum can provide discomfort to patients. Moreover, while there are now different sizes of speculums offered for an examination, it can be hard to determine the correct size for a patient as the size of the patient does not necessarily correlate with the size of the speculum that should be used.

An additional drawback to the traditional speculum design is that speculums are traditionally made of metal, though some made with disposable plastic have been increasing in use. When the speculum is made of metal, it can feel cold to the patient upon entry to the vaginal cavity, especially in comparison to the internal temperatures of the body, which can result in discomfort for the patient during the procedure. This may result in the patient tensing up and making the procedure more painful. Even when made of plastic, the design of the speculum is generally the same as the traditional design (but for some differences that may exist in the locking mechanisms, wall thicknesses, consistencies between the types of plastic, etc.), meaning that even plastic speculums may face some of the same drawbacks as traditional speculums.

Embodiments herein generally relate to accessories to improve speculum devices, components of the same, and methods of making and using the same. The devices and components overcome many drawbacks of existing speculum devices and/or they provide new improvements that have not been previously seen. For example, described herein according to some embodiments are speculum accessories that minimize discomfort for the patient, while providing improved accessibility and visibility for the practitioner. In one aspect, an insertable sleeve accessory is configured for insertion into the vagina of a patient, either by the patient or the provider (e.g., doctor, nurse, mid-wife). This can be coupled with an insertion portion of a speculum that is subsequently inserted into the vagina such that at least a portion of the sleeve covers the insertion portion of the speculum. The insertable sleeve may be used with either an existing speculum design or an updated speculum design.

SUMMARY OF THE INVENTION

One embodiment relates to an insertable sleeve for use with a medical speculum. The insertable sleeve includes a cylindrical sleeve body including an outer surface and an inner surface, the inner surface defining a hollow sleeve channel, and at least one open end. The cylindrical sleeve body is configured to be inserted into a vaginal cavity of a patient. The sleeve body is further configured to receive an insertion portion of a medical speculum in the hollow sleeve channel subsequent to being inserted into the vaginal cavity.

Another embodiment relates to a kit. The kit includes a speculum, and the speculum includes a handle and an insertion portion, the insertion portion including an upper bill and a lower bill coupled to the handle. The kit also includes an insertable sleeve. The insertable sleeve includes a cylindrical sleeve body including an outer surface, an inner surface, the inner surface defining a hollow sleeve channel, and at least one open end. The cylindrical sleeve body is configured to be inserted into a vaginal cavity of a patient. The sleeve body is further configured to receive the insertion portion of the speculum in the hollow sleeve channel subsequent to being inserted into the vagina. The kit further includes an applicator configured to carry the sleeve body and facilitate insertion of the sleeve body into the vaginal cavity.

Another embodiment relates to a method of preparing a speculum for a medical procedure. The method includes providing an insertable sleeve. The insertable sleeve includes a cylindrical sleeve body comprising an outer surface, an inner surface, the inner surface defining a hollow sleeve channel, and at least one open end. The cylindrical sleeve body is configured to be inserted into a vaginal cavity of a patient. The sleeve body is further configured to receive a pair of bills of a medical speculum in the hollow sleeve channel subsequent to being inserted in the vaginal cavity. The method also includes positioning the sleeve body in the vaginal cavity of the patient, and positioning the pair of bills of the medical speculum inside the sleeve body positioned within the vaginal cavity of the patient.

Another embodiment relates to a method of performing a vaginal examination or medical procedure on a patient, comprising, providing an insertable sleeve device; inserting the sleeve device into the vagina of the patient; inserting a speculum into an opening in the sleeve device; and performing the examination or medical procedure.

Another embodiment relates to a method of minimizing side wall encroachment or pinching in a vaginal examination or procedure, comprising, providing an insertable sleeve device according to one or more of the embodiments in the specification; inserting the sleeve into the vagina of the patient; inserting a speculum into an opening in the sleeve device; and performing a vaginal examination or medical procedure such that when the speculum is opened or closed, side wall encroachment is minimized, reduced or avoided, or pinching of sidewall tissue is reduced, minimized or avoided during use of the speculum device for an examination or medical procedure.

DETAILED DESCRIPTION

Figure 1:
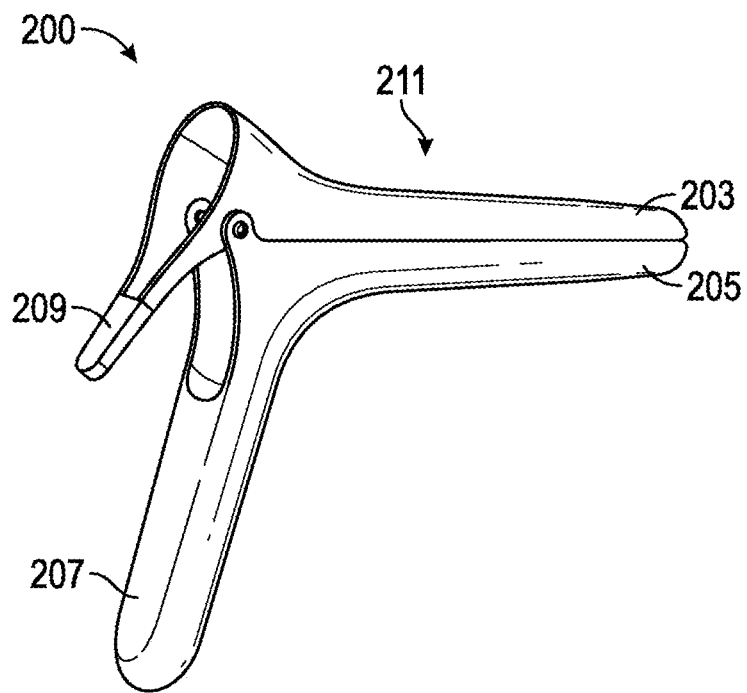
FIG. 1 is a side perspective view of a medical speculum on which an insertable sleeve accessory according to various embodiments can be used.

In the following detailed description, reference is made to the accompanying drawings, which form a part of the present disclosure. In the drawings, similar symbols typically identify similar components, unless context dictates otherwise. The illustrative embodiments described in the detailed description, drawings, and claims are not meant to be limiting. The detailed description is intended as a description of exemplary embodiments and is not intended to represent the only embodiments which may be practiced. The term "exemplary," as used herein, means "serving as an example, instance, or illustration," and should not necessarily be construed as preferred or advantageous over other embodiments. Other embodiments may be utilized, and other changes may be made, without departing from the spirit or scope of the subject matter presented herein. It will be readily understood that the aspects of the present disclosure, as generally described herein and illustrated in the Figures, can be arranged, substituted, combined, and designed in a wide variety of different configurations, all of which are explicitly contemplated by and form part of this disclosure.

Referring to the figures generally, an insertable sleeve accessory for a medical speculum is shown. The insertable sleeve accessory may be used on any traditional speculum or any new or updated speculum design, including speculums that may be specifically designed for use with the insertable sleeve accessory according to the present embodiments. The insertable sleeve has an expandable body portion and is configured to be removably attached to an insertion portion of a speculum. In certain uses, a practitioner may be able to select a speculum with a narrower profile than the practitioner would regularly select because the insertable sleeve reduces some of the previously described shortcomings of the traditional speculum design, for example, the problem of vaginal side wall tissue falling into the user's line of sight during use.

The insertable devices according to some embodiments can provide one or more advantages. For example, the insertable sleeve can be inserted by a patient of a professional conducting an obstetric or gynecologic procedure or examination. That flexibility can be empowering and advantageous, for example, for young patients not familiar with the process, patients that may have experienced a trauma, or those that may have heightened sensitivity to contact by a third party. In that and other ways, the devices may reduce anxiety that occurs with such procedures. The devices may also be produced in a variety of sizes, which may or may not correspond to a variety of correspondingly sized speculums. In this way, the size of either or both of the insert and the speculum can be specified to and appropriate for the particular patient, which can alleviate undue discomfort associated with the procedure. The devices may additionally provide the advantages of temperature insulation, for example, minimizing the shock of a cold, bare metal speculum by providing a covering for the speculum. Further, the devices provide relief from tissue and/or pubic hair pinching by preventing tissue and/or hair from entering between the blades of the speculum while the blades of the speculum are open, further alleviating the discomfort associated with the procedure. From the practitioner's perspective, the devices may provide vaginal side wall support, enhancing the visibility of the vaginal walls. Moreover, the sleeves (with or without an applicator) may be packaged individually in order to maximize cleanliness and sterility. Other potential, non-limiting advantages are described herein.

Referring now to FIG. 1, a two-blade speculum is shown according to an exemplary design. As shown, the speculum 200 has an upper bill 203 and a lower bill 205, a handle 207, and a lever 209. The upper bill 203 and the lower bill 205 together comprise an elongated insertion portion 211. The insertion portion 211, which is expandable as described herein, may be inserted into the vaginal cavity of a female patient. During insertion, the upper bill 203 and the lower bill 205 are in a closed position, wherein there is a minimal amount of space between the two bills. Once inserted and in order to dilate the vaginal cavity, the bills 203 and 205 are separated into an open position by pressing the lever 209 towards the handle 207. The speculum 200 may be made of any sturdy biomaterial including metals and plastics.

Figure 2A:
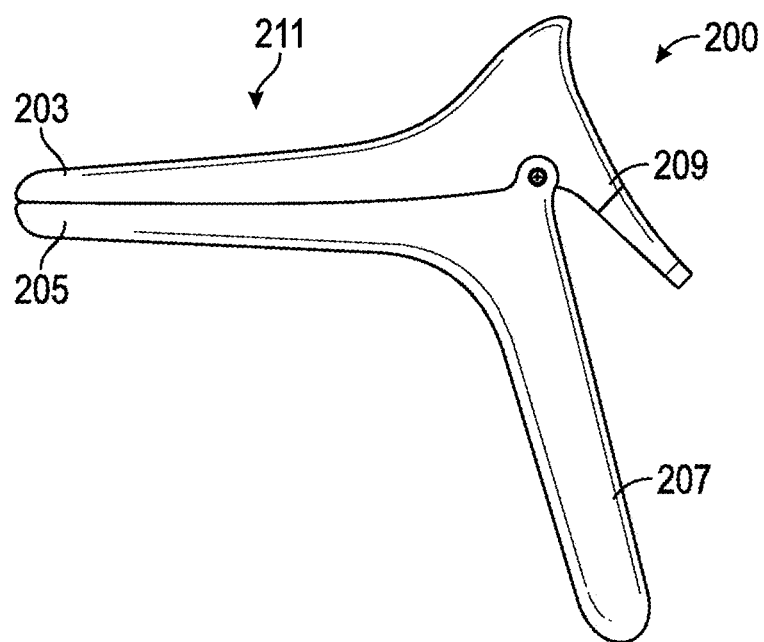
FIG. 2A is a side view of the medical speculum of FIG. 1.

Referring now to FIG. 2A, a side view of speculum 200 is shown. The upper bill 203 and the lower bill 205 may be configured in such a way that when in the closed position, the upper bill 203 and the lower bill 205 are wider near the handle 207 than near a body or end of the insertion portion 211, i.e., the bills 203 and 205 distend quickly to create somewhat of a cone shape near the handle 207, as shown in the side view of FIG. 2A. The bills 203 and 205 may maintain a constant shape after the cone, forming the elongated insertion portion 211. The upper bill 203 and the lower bill 205 of the elongated insertion portion 211 may have a uniform width or diameter as the bills 203 and 205 extend away from the handle 207. In other embodiments, the proximal portion of the bills 203 and 205 near the handle 207 may be up to two times wider than the distal end of the bills 203 and 205.

Figure 2B:
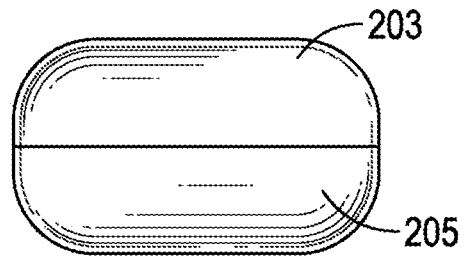
FIGS. 2B-2D are front views of the bills of the speculum of FIGS. 1 and 2A, according to various embodiments.
Figure 2C:
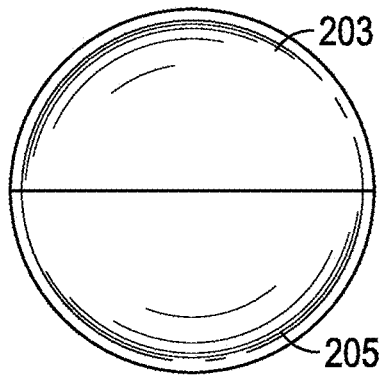
Figure 2D:
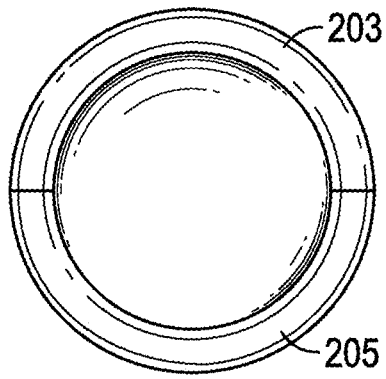

As illustrated in FIGS. 2B-2D, the bills 203 and 205 may be formed in various shapes. As seen in the front view of the bills 203 and 205 shown in FIG. 2B, the elongated insertion portion 211 may have a width that is larger than a height of the elongated insertion portion 211, creating an oblong shape when viewed from the front. Alternatively, in another embodiment, the bills 203 and 205 may each have a semi-circular cross section along the length of the bills 203 and 205 such that when the bills 203 and 205 are closed, a circular shape is formed when the bills 203 and 205 are viewed from the front, as seen in FIG. 2C. In yet another embodiment, the bills 203 and 205 may be "hollow" with outer inner edges that are circular such that when the bills 203 and 205 are in the closed position and viewed from the front, a cross section of the bills 203 and 205 is a ring shape, as seen in FIG. 2D. Beneficially, a ring-shaped cross section of bills 203 and 205 may provide a larger viewing opening for a user when the bills 203 and 205 are in the open position.

Referring back to FIG. 2A, at a distal end of the elongated insertion portion 211, away from the proximal handle 207, the bills 203 and 205 may be rounded (e.g., the bills 203 and 205 may each be rounded, the ends of bills 203 and 205 closed together may form a rounded end, etc.). A rounded end may provide more comfort to a patient while receiving the speculum 200 in a cavity. The bills 203 and 205 may also be configured such that when in the closed position, the end of each bill 203 and 205 do not abut one another, creating a gap which helps to prevent tissue from becoming lodged in between the bills 203 and 205. In one embodiment, the bills 203 and 205 may be of the same length such that when the bills 203 and 205 are closed, they form a smooth, continuous end to the insertion portion 211. Alternatively, in another embodiment, one of the bills 203 and 205 may be longer than the other, such that when the bills 203 and 205 are in the closed position, the longer bill juts out from beneath or above the other bill.

As shown in FIG. 2A, the handle 207 includes an upper portion and a lower portion. The upper portion of the handle 207 is coupled to bills 203 and 205. The lower portion provides a location for the user to hold the speculum 200. Coupled to the handle 207 or the bills 203 and 205 is a lever 209. The lever 209 includes a mechanism for opening and closing bills 203 and 205. While the lever 209 is shown to be coupled to the upper bill 203, the lever 209 may be coupled to the handle 207 or the bills 203 and 205 at any location. In some embodiments, the speculum 200 may also include a mechanism for locking the bills 203 and 205 into an open position. As an example, the user may press a button on the speculum once the user moves the bills 203 and 205 into a desired open position via the lever 209, the button locking the bills 203 and 205 into that open position. To close the bills 203 and 205, the user may press the button again, thereby deactivating the locking mechanism and allowing the user to move the bills 203 and 205 to the closed position via the lever 209. In this example, the button may be a toggle switch, where pressing one side of the toggle switch locks the bills and pressing the other side of the toggle switch releases, or unlocks, the bills. As another example, the bills 203 and 205 may automatically lock into the open position once the user moves the lever 209 past a certain "locking point." To unlock the bills 203 and 205, the user may move the lever 209 down past the locking point or, alternatively, up further past the locking point, at which point the locking mechanism may deactivate and the user may close the bills 203 and 205 by the lever 209.

Though specific reference is made in this specification to the elements or features of speculum 200, it is understood that the accessory or modifier elements described herein may be used with any speculum having an elongated and expandable insertion portion, such as any two blade speculum design. The features herein used to describe speculum 200 may also be present on any other speculum on which the accessory or modifier elements described herein may be used.

According to various embodiments, an insertable sleeve accessory is used to at least partially cover and surround an insertion portion of a speculum, such as the insertion portion 211 of the speculum 200. The insertable sleeve accessory is first positioned in the vagina, and once positioned, the speculum is inserted through the insertable sleeve already in place in the vagina.

Figure 3:
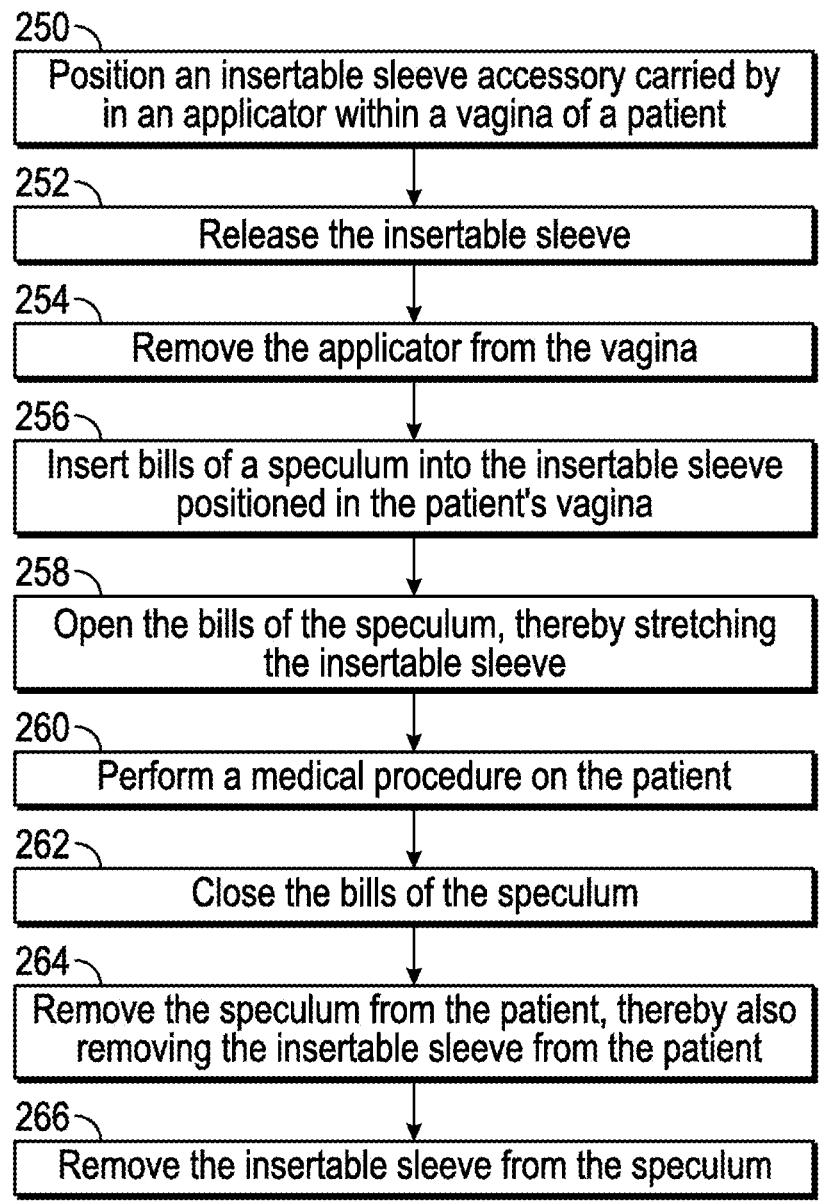
FIG. 3 is a flow diagram of a process of using an insertable sleeve accessory with a speculum, according to one embodiment.

FIG. 3 shows a flow diagram illustrating a process for using an insertable sleeve accessory, according to one embodiment. At step 250, an insertable sleeve accessory carried by an applicator is positioned within a vagina of a patient. The user in step 250 may be the patient herself, who positions the applicator, carrying the insertable sleeve accessory, within her own vagina. At step 252, the user releases the insertable sleeve from the applicator. Again, the user may be the patient, who uses the applicator to release the insertable sleeve into her own vagina. In some embodiments, the applicator may include a delivery mechanism (e.g., similar to a tampon) whereby the user may release the insertable sleeve. At step 254, the user removes the applicator from the patient's vagina. When the user removes the applicator, the insertable sleeve remains behind in the patient's vagina. In this way, a patient may position and release the insertable sleeve in her vaginal cavity before a practitioner uses a speculum to conduct a medical examination or procedure involving the vaginal cavity. Alternatively, a medical practitioner may serve as the user and perform any of steps 250, 252, and 254.

At step 256, the bills of a speculum are inserted into the insertable sleeve positioned in the patient's vagina. The user at step 256 may be a medical practitioner conducting a medical examination or procedure with a speculum, such as speculum 200. As such, the practitioner may insert the bills 203 and 205 of the insertion portion 211 into the insertable sleeve previously positioned and released in the patient's vagina at steps 250 and 252, thereby positioning the insertable sleeve on the insertion portion 211 of the speculum 200. At step 258, the user opens the bills of the speculum, such as bills 203 and 205 of speculum 200, thereby stretching the insertable sleeve. For example, the user, who may be a practitioner, may open the speculum by applying a force to the lever 209 of speculum 200. When the speculum is opened, the bills 203 and 205 move away from each other, causing the insertable sleeve positioned on the bills 203 and 205 to stretch.

At step 260, the user, such as a medical practitioner, performs a medical examination or procedure on the patient by using the speculum in the open position. The medical procedure may be any obstetric or gynecological procedure, such as an examination of the vaginal cavity, a Pap smear, an insertion or removal of an intrauterine device (IUD), an insemination, a sexually transmitted infection (STI) testing, a tissue collection, a biopsy, or an electrosurgery. After the user completes the medical procedure, the user closes the bills of the speculum, as shown at step 262. The user may do this, for example, by applying an opposite force to the lever 209 of speculum 200. Additionally, the user may need to deactivate a locking mechanism of the speculum that is keeping the bills of the speculum in an open position before the user may be able to close the speculum.

At step 264, the user removes the speculum from the patient. In doing so, the user also removes the insertable sleeve from the patient, as the insertable sleeve is now positioned on the speculum as a result of step 256. At step 266, the user removes the insertable sleeve from the speculum by, e.g., rolling the insertable sleeve off, pushing the insertable sleeve off, etc. Alternatively, the user may use a removal device that helps the user remove the insertable sleeve from the insertion portion of the speculum.

FIGS. 4 through 8 illustrate portions of the processes 250-266 described above. FIG. 4A depicts an embodiment of an insertable sleeve accessory, shown as insertable sleeve accessory 301, being released from an applicator carrying the insertable sleeve accessory 301, shown as applicator 303. In some embodiments, the insertable sleeve 301 has a cylindrical sleeve body. By "cylindrical" it is meant that the sleeve body has a continuous, longitudinal shape that surrounds a hollow area (i.e., a hollow sleeve channel) within an inner wall or surface of the cylinder. The cylindrical sleeve body is not limited to a circular cylinder and may instead have a cross-sectional shape that is a triangle, a square, a rectangle, a hexagon, a circle, an oval, and so on.

In the embodiment shown, the insertable sleeve 301 has a cylindrical shape with a proximal opening 304 and a distal opening 305. In other embodiments, an insertable sleeve 301 may include only one opening (e.g., only a proximal opening). The insertable sleeve 301 may be configured to receive an insertion portion of a speculum, such as insertion portion 211 of speculum 200, through the proximal opening 304. In the embodiment shown, the shape of the insertable sleeve 301 substantially matches the shape of bills 203 and 205, which may be in one of the shapes shown in FIGS. 2B-2D or may be in another shape. As such, the cylindrical body of the insertable sleeve 301 may have a uniform width or diameter between the proximal end 304 of the sleeve body and the distal end 305 of the sleeve body while the insertable sleeve 301 is in an un-stretched or unexpanded state, to match a uniform width or diameter of the bills 203 and 205 extending away from the handle 207. In one embodiment, the uniform diameter of the cylindrical body of the sleeve 301 may range between 0.25 and 4.0 inches. In other embodiments, the insertable sleeve 301 may comprise a different natural shape than the shape of the bills 203 and 205 (e.g., an accordion shape, a fluted shape, a webbed shape, etc.), and may also have a non-uniform width or diameter ranging between 0.25 and 4.0 inches when in an un-stretched or unexpanded state.

The applicator 303 may assist the user with inserting and positioning the insertable sleeve 301 in the vagina of the patient. In some embodiments, the applicator 303 may consist of multiple pieces, such as a piece that surrounds an outer surface of the insertable sleeve 301 and a piece that fits inside the insertable sleeve 301. For example, the embodiment of the applicator 303 shown in FIG. 4 consists of a sleeve tube 303a and a plunger 303b. The sleeve tube 303a fits over the outer surface of the insertable sleeve 301, while the plunger 303b fits inside the hollow sleeve channel of the insertable sleeve 301. In this way, the sleeve tube 303a, the insertable sleeve 301, and the plunger 303b may be coupled together, with the plunger 303b inserted into the hollow sleeve channel of the insertable sleeve 301 and the insertable sleeve 301 inserted into the hollow cylindrical body of the sleeve tube 303a. In other embodiments, however, the applicator 303 may consist of only one piece (e.g., the applicator 303 may only be a plunger or the applicator 303 may only be a sleeve tube).

Figure 4A:
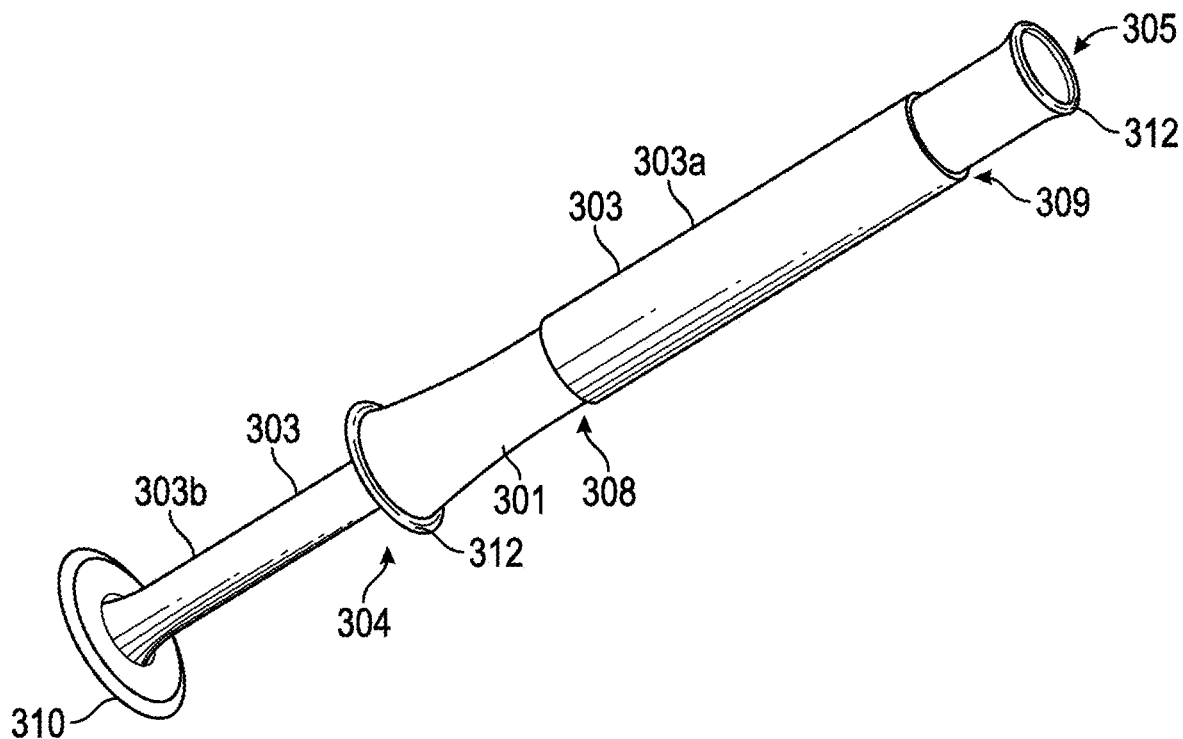
FIG. 4A is a side perspective view of an applicator carrying an insertable sleeve accessory, according to an exemplary embodiment.

Referring to the tube-and-plunger embodiment of the applicator 303 shown in FIG. 4A, the sleeve tube 303a may include an elongated, cylindrical body with two open ends, proximal end 308 (i.e., the end designed to point out of the patient's vagina) and distal end 309 (i.e., the end designed to point into the patient's vagina). Similar to the insertable sleeve 301, by "cylindrical" it is meant that the body of the sleeve tube 303a has a continuous, longitudinal shape that surrounds a hollow area within an inner wall or surface of the cylinder. However, the cylindrical body of the sleeve tube 303a is not limited to a circular cylinder and may instead have a cross-sectional shape that is a triangle, a square, a rectangle, a hexagon, a circle, an oval, and so on. Additionally, in other embodiments, the sleeve tube 303a may include only one open end (e.g., only a proximal end 308 of the sleeve tube 303a may be open), and/or one or more openable ends (e.g., one or more ends that may move from a closed position to an open position, similar to distal end 409 of insertable sleeve 401 shown in FIG. 5A).

The sleeve tube 303a may be designed to fit the shape of the outer surface the insertable sleeve 301. For example, the sleeve tube 303a embodied in FIG. 4A has a circular cross-section fit the circular cylindrical sleeve body of the insertable sleeve 301. In other embodiments, the sleeve tube 303a may take on a different shape from the insertable sleeve 301. The sleeve tube 303a may be configured to receive the insertable sleeve 301 into the hollow area within the cylindrical body of the sleeve tube 303a by either the open proximal end 308 or the open distal end 309. Additionally, the sleeve tube 303a may contain the full length of the insertable sleeve 301, or only a portion of the insertable sleeve 301 (e.g., as shown in FIG. 4A).

The plunger 303b of applicator 303 may include an elongated, cylindrical body configured to fit inside the insertable sleeve 301. By "cylindrical" it is meant here that the body of the plunger 303b has a continuous, longitudinal shape, though the plunger 303b is not limited to a circular cylinder. As with the sleeve tube 303a, the plunger 303b may instead have a cross-sectional shape that is a triangle, a square, a rectangle, a hexagon, a circle, an oval, and so on. The body of the plunger 303b may be designed to fit the shape of the inner surface of the insertable sleeve 301. For example, the plunger 303b embodied in FIG. 4A has circular cross-section such that it conforms to the circular hollow sleeve channel of the insertable sleeve 301. In other embodiments, however, the plunger 303a may take on a different shape from the insertable sleeve 301. In some embodiments, the plunger 303b further includes a flared end (e.g., an end that distends outward from the cylindrical body of the plunger 303b), shown in FIG. 4A as flared end 310. The flared end 310 may be beneficial to a user by providing the user with a larger area by which to apply a force to the plunger 303b in order to release the insertable sleeve 301 from the applicator 303 once positioned within the patient's vagina. The plunger 303b may be solid throughout the cylindrical body, or the plunger 303b may be hollow.

Beneficially, the applicator serves as an additional means of sanitation and comfort for the patient, as the patient knows that an outer portion of the insertable sleeve 301 to be positioned in the patient's vagina has had limited, if any, contact with the hands of anyone handling the insertable sleeve 301 or any other item which may transfer dirt, germs, or otherwise unsanitary elements to an outer surface of the insertable sleeve 301. Furthermore, the applicator 303 allows for a do-it-yourself step (e.g., at steps 250, 252, and 254 of FIG. 3) before a medical practitioner performs a gynecological or other intrusive medical procedure with a speculum, such as speculum 200. The insertable sleeve 301 thus allows the patient to be more actively involved in the procedure and provides the patient with the opportunity to perform the initial penetration into the body, both desensitizing the tissues and also reducing patient anxiety related to use of the speculum 200.

As discussed above, FIG. 4A illustrates the insertable sleeve 301 in the process of being deployed by the applicator 303. The insertable sleeve 301 contained by applicator 303 can be inserted into the vaginal cavity of a patient, by the patient herself or by a practitioner, in a similar fashion to a tampon, a process that the patient is likely familiar with. To insert the insertable sleeve 301, the user, who may be a patient or a medical practitioner, holds the cylindrical body of the sleeve tube 303a while pushing the sleeve tube 303a, with the distal end 309 of the sleeve tube facing inward towards the patient's body, into the patient's vagina. Because the sleeve tube 303a is coupled to the insertable sleeve 301, which in turn is coupled to the plunger 303b, pushing the sleeve tube 303a into the patient's vagina also pushes the insertable sleeve 301 and the plunger 303b into the patient's vagina. Once the sleeve tube 303a has reached the desired position within the vaginal cavity, the user pushes or otherwise deploys the insertable sleeve 301 into the patient's vagina. For example, the user may apply a force to the flared end 310 of the plunger 303b, thereby causing the plunger 303b to push the insertable sleeve 301 through the distal end 309 of the sleeve tube 303a and further into the patient's vagina. In other embodiments of the applicator 303, the applicator 303 may include a different release mechanism that releases, ejects, disengages, or otherwise causes the separation of the insertable sleeve 301 from the applicator 303.

Figure 4B:
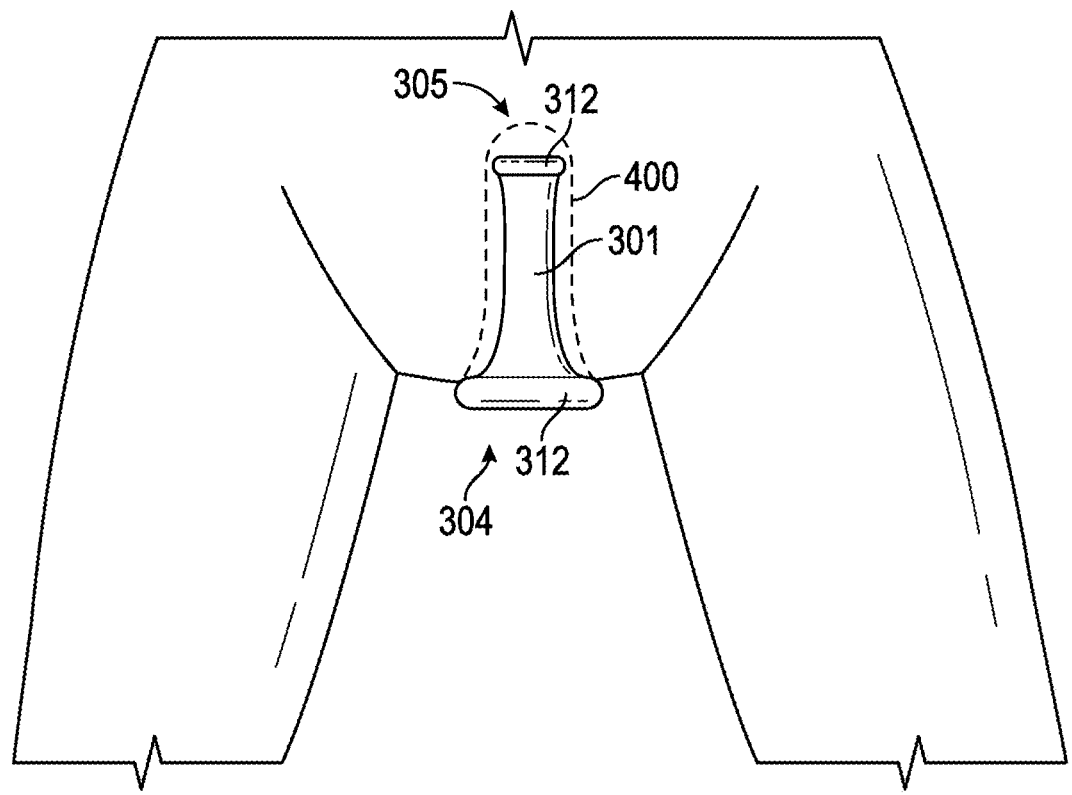
FIG. 4B is a front view of the insertable sleeve accessory of FIG. 4A having been inserted into the vagina of a patient.

As shown in FIG. 4B, once the insertable sleeve 301 has been positioned and released into the patient's vagina, shown as vaginal cavity 400, the applicator 303 is removed from the patient's vagina, leaving the insertable sleeve 301 deployed in the patient's vagina. The applicator 303 may be disposable after it has delivered the insertable sleeve 301. Alternatively, one or more components of the applicator 303 (e.g., sleeve tube 303a and/or plunger 303b) may be reused after, e.g., sterilization.

The insertable sleeve 301 may be made of one or more compliant or partially compliant materials, such as latex, vinyl, natural and synthetic rubbers, silicone, nylon, polyethylene, polyurethane, polypropylene, and non-degradable or degradable elastomers. In preferred embodiments, the insertable sleeve 301 may be made of a polyisoprene (PI), a polyurethane (PU), a thermoplastic polyurethane (TPU), a styrene copolymer (SBS), and/or a thermoplastic elastomer (TPE). The material of the insertable sleeve 301 may range from completely transparent to translucent or frosty to opaque. Alternatively, the insertable sleeve 301 may include a finish that ranges from completely transparent to translucent or frosty to opaque. Different finishes may be used for different types of gynecological examinations or procedures. For example, a thicker and/or more opaque sleeve may be used for a surgical procedure, such as an electrosurgery, while a thinner and/or more clear sleeve may be used for a gynecological examination or procedure. The applicator 303, including the sleeve tube 303a and/or the plunger 303b, may be made of similar materials, or it may be made of another material such as paperboard, corrugated fiberboard, polycarbonate or other plastics, and other less complaint materials. Alternatively, different components of the applicator 303 may be made of different materials. For example, the sleeve tube 303a of the applicator may be made of a different material from the plunger 303b.

The insertable sleeve 301, or a portion of the insertable sleeve 301, may optionally be coated with one or more bioactive or therapeutic agents, lubricants, powders, and/or surface finishes. Additionally, or alternatively, one or more components of the applicator 303 (e.g., the sleeve tube 303a and/or the plunger 303b), or a portion of one or more components of the applicator 303, may optionally be coated with one or more bioactive or therapeutic agents, lubricants, powders, and/or surface finishes. Examples of suitable bioactive or therapeutic agents include, but are not limited to, hormonal and non-hormonal contraceptive agents, cancer screening agents, vaginal spermicides, vaginal microbicides, antibacterial agents, antifungal agents, antiviral agents, anti-HIV agents, and cancer treatment agents, or combinations thereof. The bioactive or therapeutic agents may be in any suitable formulation that may be applied to the surface of a vaginal speculum, such as a liquid, gel and powder.

In some embodiments, lubricants may be applied to at least a portion of an inner surface of the insertable sleeve 301 and/or to an outer surface of the insertable sleeve 301. When applied to the inner surface of the insertable sleeve 301, the lubricant may, for example, assist in inserting one or more components of the applicator 303 (e.g., plunger 303b) into the hollow sleeve channel of the insertable sleeve 301, assist in releasing the insertable sleeve 301 from the applicator 303 (e.g., allow the plunger 303b to be more easily withdrawn from the hollow sleeve channel of the insertable sleeve 301), and so on. When applied to the outer surface of the sleeve, the lubricant may, for example, help the insertable sleeve 301 be more easily inserted into the vagina of the patient, assist in releasing the sleeve 301 from the applicator (e.g., allow the sleeve tube 303a to be more easily withdrawn from the outer surface of the insertable sleeve 301), and so on. In other embodiments, the lubricant on the interior surface and/or exterior surface of the insertable sleeve 301 may instead be, or may be combined with, a powder applied to the insertable sleeve 301 and/or a surface texture finished into a material of the insertable sleeve 301. The powder and/or surface texture may likewise, for example, assist the user in deploying the insertable sleeve 301 by the applicator 303, help the insertable sleeve 301 be more easily inserted into the vagina of the patient, assist in releasing the insertable sleeve 301 from the applicator 303, and so on.

In other embodiments, a lubricant, a powder, a surface texture, and/or a combination thereof may be applied to an interior surface and/or an outer surface of one or more components of the applicator 303 (e.g., the outer surfaces and/or the inner surfaces of sleeve tube 303a and/or the plunger 303b). When applied to an outer surface of the sleeve tube 303a, the lubricant, powder, and/or surface texture may, for example, assist the user with inserting the sleeve tube 303a containing the insertable sleeve 301 into the vagina of the patient, assist the user in removing the sleeve tube 303a from the vagina of the patient once the insertable sleeve 301 is released, and so on. When applied to an inner surface of the sleeve tube 303a, the lubricant, powder, and/or surface texture may, for example, assist the user in releasing the insertable sleeve 301 from the sleeve tube 303a, assist the user in removing the sleeve tube 303a from the insertable sleeve 301 once the insertable sleeve 301 is released, and so on. When applied to an outer surface of the plunger 303b, the lubricant, powder, and/or surface texture may, for example, assist the user in deploying the insertable sleeve 301 within the vaginal cavity by the plunger 303b, assist the user in removing the plunger 303b from the hollow sleeve channel of the insertable sleeve 301 once the insertable sleeve 301 has been deployed, and so on.

In one embodiment, the insertable sleeve 301 and/or one or more components of the applicator 303 may come with lubricant and/or powder pre-applied. In other embodiments, the insertable sleeve 301, as well as or alternatively one or more components of the applicator 303, may come in a kit with lubricant and/or powder included for the user to apply, may come with instructions that recommend types or brands of lubricants and/or powders for the user to apply to create the beneficial effects discussed above, etc.

One or more components of the applicator 303, such as sleeve tube 303a and/or plunger 303b, may include ribbed details or other gripping elements. As an example, ribbed details may help the applicator 303 remain coupled to the insertable sleeve 301 during insertion of the applicator 303 into the vagina of the patient. Alternatively, ribbed details or other gripping elements positioned on an outside surface of the applicator 303 may help the user with grasping the applicator 303 during insertion. In various embodiments, the sleeve tube 303a may include ribbed details on the proximal end 308, on the distal end 309, on the proximal end 308 and the distal end 309, or distributed throughout the cylindrical body of the sleeve tube 303a. In other embodiments, the plunger 303b may, additionally or alternatively, include ribbed details on its proximal end, on its distal end, on its proximal end and its distal end, or distributed throughout the cylindrical body of the plunger 303b. In some embodiments, the ribbed details may instead be, or may be combined with, texture differences provided on inner and/or outer surfaces of the applicator 303 and/or other gripping elements (e.g., flanges, ridges, bumps, dimples, and/or other indentations or extensions that increase the resistance against slipping) positioned on inner and/or outer surfaces of the applicator 303.

The insertable sleeve 301 may likewise include ribbed details that help the insertable sleeve 301 remain coupled to the applicator 303 and/or help the insertable sleeve 301 grip the speculum once the speculum is inserted into the insertable sleeve 301. In one embodiment, the ribbed details on the insertable sleeve 301 may be limited to a portion of the insertable sleeve 301 designed to be secured to the smaller, narrower, distal end of the insertion portion 211 of the speculum 200 (i.e., near the distal opening 305 of the insertable sleeve 301). In other embodiments, the ribbed details may, additionally or alternatively, be limited to a portion of the insertable sleeve 301 designed to be secured to the larger, proximal end of the insertion portion 211 (i.e., near the proximal opening 304 of the insertable sleeve 301), or be distributed throughout the length of the insertable sleeve 301. In some embodiments, the ribbed details may instead be, or may be combined with, texture differences provided on an inner and/or an outer surface of the insertable sleeve 301, and/or gripping elements (e.g., flanges, ridges, bumps, dimples, and/or other indentations or extensions that increase the resistance against slipping) positioned on an inner and/or outer surface of the insertable sleeve 301.

As discussed, the insertable sleeve 301 embodied in FIGS. 4A and 4B includes two open ends (i.e., proximal opening 304 and distal opening 305), though other embodiments of the insertable sleeve 301 may include only one open end (e.g., only proximal opening 304). One or both of the proximal opening 204 and the distal opening 305 may be lined with a ridged finish, shown in FIGS. 4A and 4B as end rings 312. The ridged finish may be provided to give the user ridges to aid the user in positioning the insertable sleeve 301 onto the applicator 303, to finish the ends of the insertable sleeve 301 so that the ends of the insertable sleeve 301 are less easily ripped or otherwise damaged, to provide additional tension to adhere the insertable sleeve 301 to the plunger 303b and/or the insertion portion 211 of the speculum 200, to retain the insertable sleeve 301 in the body, and so on. Importantly, a ridged finish on the proximal opening 304 of the insertable sleeve 301 may help keep the proximal opening 304 open, once the insertable sleeve 301 has been released in the patient's vagina, so that the insertable sleeve 301 may more easily receive the insertion portion 211 of the speculum 200. Additionally, a ridged finish on the distal end 305 of the insertable sleeve 301 may help retain the insertable sleeve 301 in the desired position within the patient's vagina once deployed, help open the vaginal cavity for the obstetric or gynecological procedure being performed, and so on.

As shown in FIGS. 4A and 4B, the ridged finish may be provided as end rings 312, which may be a rolled bead edge (i.e., similar to a condom) or may be formed from an encapsulated ring (i.e., a ring that is rolled into the end of the insertable sleeve 301 and cured). In other embodiments, the ridged finish may be provided as a dip in the material of the insertable sleeve 301, a secondary dip in another polymer material (e.g., of a different thickness, durometer, color, etc.) attached to the insertable sleeve 301, an otherwise attached or adhered secondary material that finishes the opening(s), a compressed ring rolled into the material of the sleeve body (e.g., similar to foam ring 714c shown in FIG. 7C) and so on. Alternatively, in some embodiments, the end ring 312 may be comprised of a portion of the sleeve body near the proximal opening 304 that is naturally in a rolled configuration. The rolled portion may be flattened out by an unrolling force in the proximal direction, such as by sliding the applicator 303 off of the insertable sleeve 301. The rolled portion may then resume its rolled configuration after the applicator 303 has passed over it, for example, as shown by the end ring 312 on the outside of the vagina in FIG. 4B.

Figure 5A:
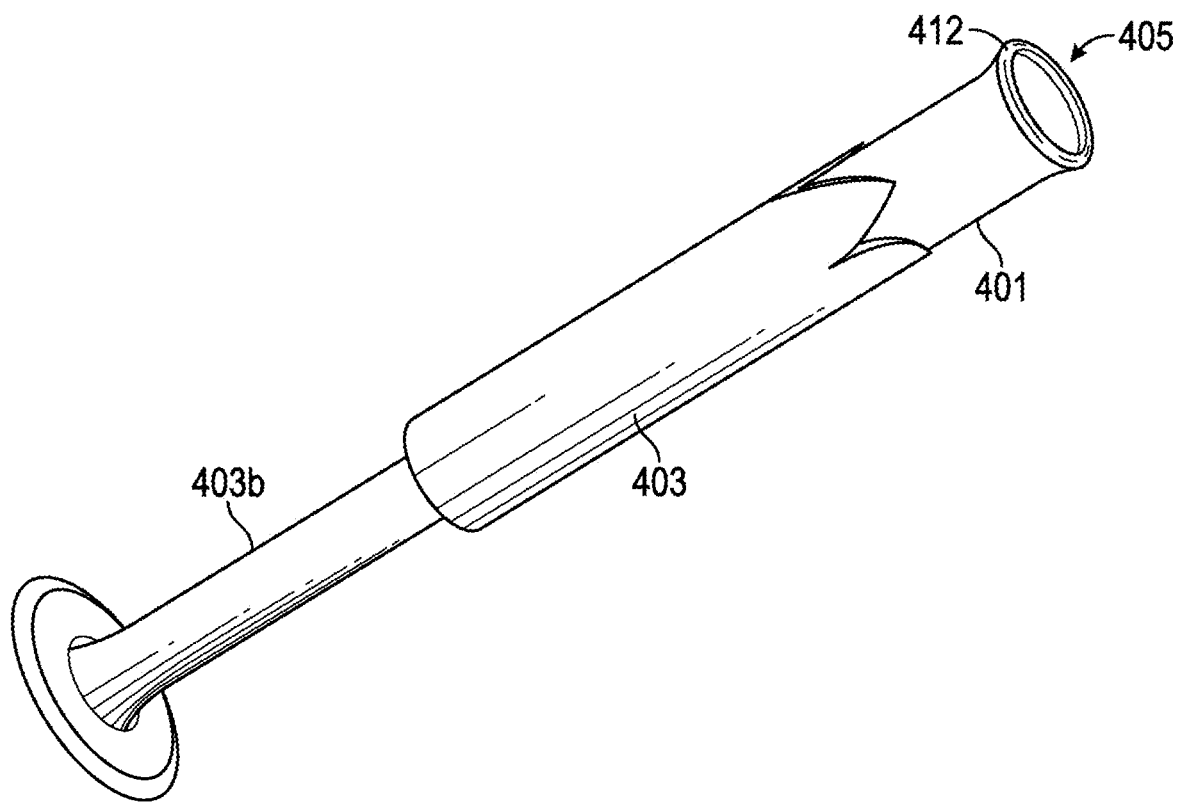
FIG. 5A is a side perspective view of an applicator carrying an insertable sleeve accessory, according to an exemplary embodiment.

FIG. 5A depicts another embodiment of an insertable sleeve accessory, shown as insertable sleeve accessory 401, being released from an applicator, shown as applicator 403. Insertable sleeve 401 is generally configured similarly to insertable sleeve 301. As shown in FIG. 5A, the insertable sleeve 401 has a cylindrical sleeve body with an outer surface and an inner surface defining a hollow sleeve channel. As embodied FIG. 5A, the insertable sleeve 401 has a circular cylindrical sleeve body, but in other embodiments the cylindrical sleeve body of the insertable sleeve 401 may have a different cross-sectional shape, such as a triangle, a square, a rectangle, a hexagon, a circle, an oval, and so on. The cylindrical sleeve body of insertable sleeve 401 has a proximal opening 404 and a distal opening 405. The insertable sleeve 401 may be configured to receive an insertion portion of a speculum, such as insertion portion 211 of speculum 200, through the proximal opening 404. In the embodiment shown, the shape of the insertable sleeve 401 substantially matches the shape of bills 203 and 205, which may be in one of the shapes shown in FIGS. 2B-2D or may be in another shape, and may have a uniform width or diameter when in an un-stretched or unexpanded state. In other embodiments, the insertable sleeve 401 may comprise a different natural shape than the shape of the bills 203 and 205 (e.g., an accordion shape, a fluted shape, a webbed shape, etc.), and may have a non-uniform width or diameter when in an un-stretched or unexpanded state.

Figure 5B:
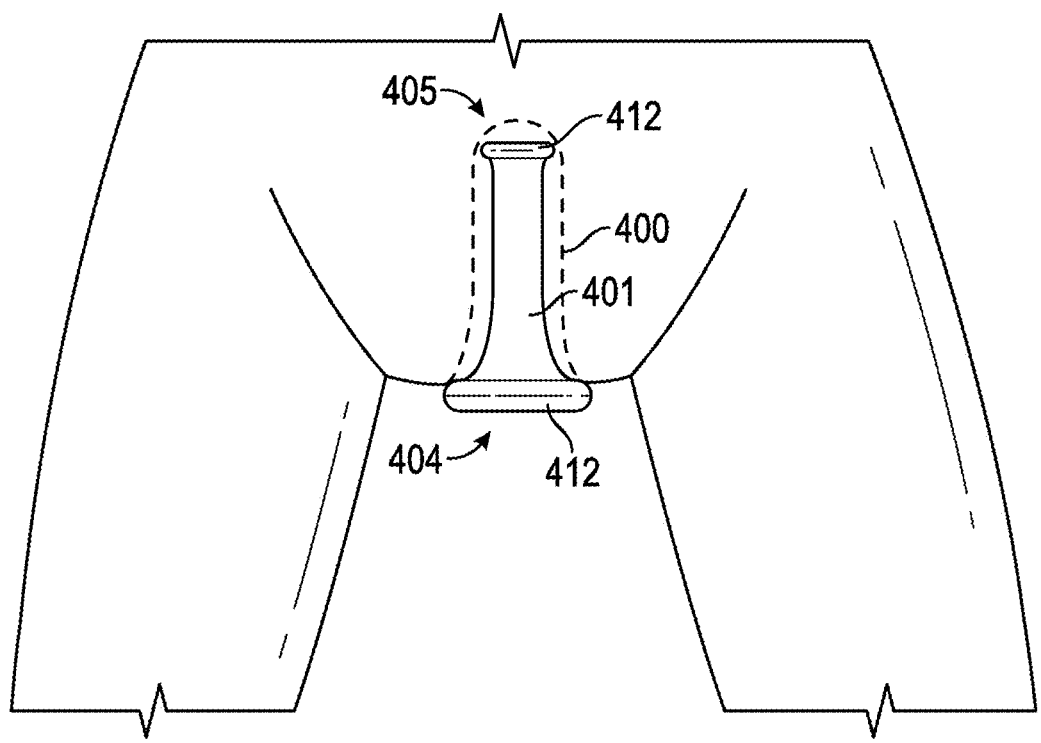
FIG. 5B is a front view of the insertable sleeve accessory of FIG. 5A having been inserted into the vagina of a patient.

Similar to insertable sleeve 301, one or both of the proximal opening 404 and the distal opening 405 of the insertable sleeve 401 may be lined with a ridged finish. In FIGS. 5A and 5B, both the proximal opening 404 and the distal opening 405 are lined with a ridged finish, shown as end ring 412. As with end rings 312, the ridged finish may aid the user in positioning the insertable sleeve 401 into the applicator 403, finish the ends of the insertable sleeve 401 so that the ends are less easily ripped or otherwise damaged, provide additional tension to adhere the insertable sleeve 401 to an insertion portion of a speculum (e.g., insertion portion 211 of speculum 200), to retain the insertable sleeve 401 in the body, and so on. Importantly, a ridged finish on the proximal opening 404 of the insertable sleeve 401 may help keep the proximal opening 404 open, once the insertable sleeve 401 has been released into a patient's vaginal cavity, so that the insertable sleeve 401 may more easily receive the insertion portion 211 of the speculum 200. In various embodiments, the end ring 412 may be provided as a rolled bead edge, formed from an encapsulated ring that is cured into the insertable sleeve 401, provided as a dip in the material of the insertable sleeve 401, provided as a secondary dip in another polymer material attached to the sleeve 401, provided as a foam ring, provided as a naturally rolled portion of the sleeve body, etc.

As with applicator 303, applicator 403 may assist the user with inserting and positioning the insertable sleeve 401 in the vagina of the patient. As shown in FIG. 5A, applicator 403 consists of one piece, a sleeve tube with flanges, that is generally similar to sleeve tube 303a discussed above. However, in other embodiments, the applicator 403 may consist of multiple pieces (e.g., similar to applicator 303 including sleeve tube 303a and plunger 303b). The applicator 403, consisting of the sleeve tube with flanges, may include an elongated, cylindrical body with one open end, shown as proximal end 408 (i.e., the end designed to point out of the patient's vagina), and one openable end, shown as distal end 409 (i.e., the end designed to point into the patient's vagina). The openable distal end 409 is configured such that the end may move from a closed position to an open position, though in other embodiments an openable end may be configured to move from an open position to a closed position. As shown in FIG. 5A, the applicator 403 has a circular cylindrical sleeve body, but in other embodiments the applicator 403 may instead have a cross-sectional shape that is a triangle, a square, a rectangle, a hexagon, a circle, an oval, and so on. Additionally, in other embodiments, the applicator 403 may include more than one open end (e.g., an open proximal end 408 and an open distal end 409), more than one openable end (e.g., an openable proximal end 408 and an openable distal end 409), or an open end and a closed end (e.g., an open proximal end 408 and a closed distal end 409, or an open distal end 409 and a closed proximal end 408).

The applicator 403 may be designed to fit the shape of the outer surface of the insertable sleeve 401. For example, the applicator 403 embodied in FIG. 5A has a circular cross-section to fit the circular sleeve body of the insertable sleeve 401. In other embodiments, the applicator 403 may take on a different shape from the insertable sleeve 401. The applicator 403 may be configured to receive the insertable sleeve 401 into the hollow area within the cylindrical body of the applicator 403 by the open proximal end 408. Additionally, the applicator 403 may contain the full length of the insertable sleeve 401, or only a portion of the insertable sleeve 401.

As discussed, the applicator 403 may include one or more openable ends. In the embodiment of FIG. 5A, the distal end 409 of applicator 403 is openable from a closed position to an open position. The distal end 409 is tapered by way of a plurality of distal flanges cut into the cylindrical body of the applicator 403, which are biased in a tapered fashion towards the center axis of the applicator 403. The tapered end provides for smooth insertion into the vagina, though in other embodiments of the applicator 403 openable ends or closed ends may be provided in a different shape (e.g., a flat surface, a gently pointed surface, etc.). The distal end 409 may be moved from a closed position to an open position when the user pushes or otherwise deploys the insertable sleeve 401 through the distal end 409, thereby opening the flanges as shown in FIG. 5A. The applicator 403 generally provides the same benefits as those discussed with respect to applicator 303 above, such as ensuring limited contact with the an outer surface of the insertable sleeve 401 before and during insertion into the patient's vagina so that the insertable sleeve 401 remains sanitary.

FIG. 5A illustrates the insertable sleeve 401 in the process of being deployed through the applicator 403. Similar to insertable sleeve 301 with applicator 303, the insertable sleeve 401 contained by applicator 403 can be inserted into the vaginal cavity of a patient, by the patient herself or the practitioner, in a similar fashion to a tampon. To insert the insertable sleeve 401, the user holds the cylindrical body of the applicator 403 while pushing the applicator 403, with the distal end 409 of the applicator 403 facing inward towards the patient's body, into the patient's vagina. When the user begins inserting the insertable sleeve 401 and the applicator 403 into the patient's vagina, the distal end 409 of the applicator 403 is in the closed position (i.e., the flanges are still biased in a tapered fashion towards the center axis of the applicator 403). As the applicator 403 is coupled to the insertable sleeve 401, pushing the applicator 403 into the patient's vagina also pushes the insertable sleeve 401 into the patient's vagina. Once the applicator 403 has reached the desired position within the vaginal cavity, the user pushes or otherwise deploys the insertable sleeve 401 through the distal end 409 of the applicator 403 by, for example, applying a force to the plunger 403b of the insertable sleeve 401 or to the distal end of the insertable sleeve 401 itself. By doing this, the user causes the flanges to open, as shown in FIG. 5A, thereby deploying the insertable sleeve 401 into the patient's vagina. In other embodiments, the applicator 403 may include a different release mechanism that releases, ejects, disengages, or otherwise causes the separation of the insertable sleeve 401 from the applicator 403.

As shown in FIG. 5B, once the insertable sleeve 401 has been positioned and released into the patient's vaginal cavity 400, the applicator 403 is removed from the patient's vagina, leaving the insertable sleeve 401 deployed in the patient's vagina. The applicator 403 may be disposable after has it has delivered the insertable sleeve 401. Alternatively, the applicator 403 may be reused after, e.g., sterilization.

The insertable sleeve 401 may be made of any of the materials described above with respect to sleeve 301, and the applicator 403 may be made of any of the materials described above with respect to applicator 303. As with insertable sleeve 301 and applicator 303, the insertable sleeve 401 and/or the applicator 403 may be coated with one or more bioactive or therapeutic agents, lubricants, powders, or surface finishes on inner and/or outer surfaces of the insertable sleeve 401 and the applicator 403. These lubricants, powders, and/or surface textures may work, for example, to help the insertable sleeve 401 more easily slide into the vagina of a patient, be more easily deployed from the applicator 403 within the vagina of the patient, be more easily decoupled from the applicator 403, and so on. Moreover, similar to insertable sleeve 301 and applicator 303, the insertable sleeve 401 and/or the applicator 403 may include ribbed details, texture differences, and/or gripping elements positioned on their inner and/or outer surfaces, for example, to help the applicator 403 remain coupled to the insertable sleeve 401 during insertion into the patient's vagina, help the insertable sleeve 401 grip a speculum inserted into hollow sleeve channel of the deployed insertable sleeve 401, and so on.

Figure 6A:
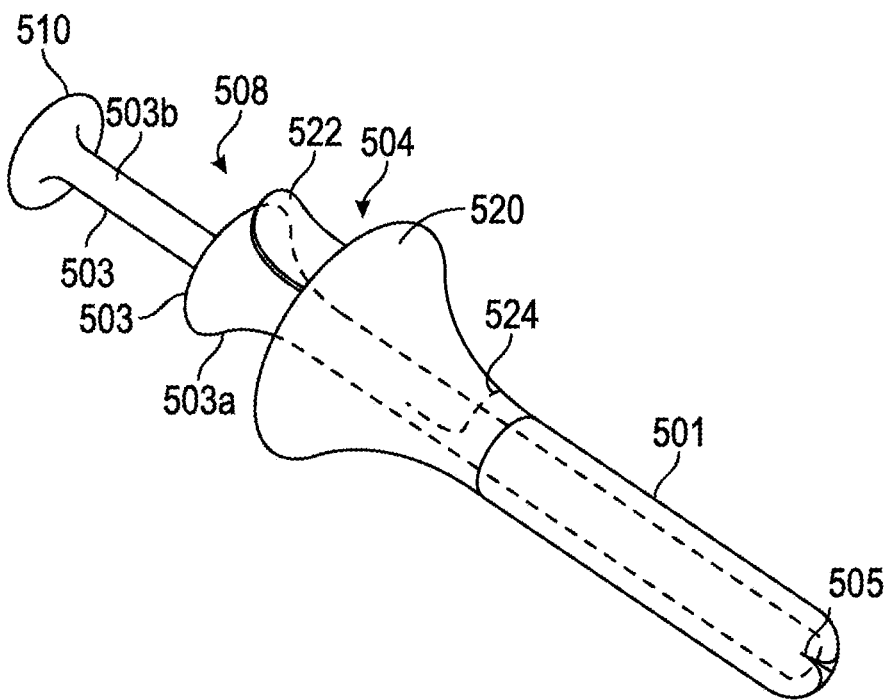
FIG. 6A is a side perspective view of an applicator carrying an insertable sleeve accessory, according to an exemplary embodiment.

FIG. 6A depicts another embodiment of an insertable sleeve accessory, shown as insertable sleeve accessory 501, prior to being released from an applicator, shown as applicator 503. Insertable sleeve 501 is generally configured similarly to insertable sleeve 301 and insertable sleeve 401 discussed above. As shown in FIG. 6A, the insertable sleeve 501 has a cylindrical sleeve body with an outer surface and an inner surface defining a hollow sleeve channel. As shown in FIG. 6A, the insertable sleeve 501 has a circular cylindrical sleeve body, but in other embodiments, the cylindrical sleeve body may instead be a different cross-sectional shape, such as a triangle a square, a rectangle, a hexagon, a circle, and oval, and so on. The cylindrical sleeve body of insertable sleeve 501 has two openings though other embodiments of the insertable sleeve 501 may include only one opening. The insertable sleeve 501 may be configured to receive an insertion portion of a speculum, such as insertion portion 211 of speculum 200, through the proximal opening 504. In the embodiment shown, the shape of the insertable sleeve 401 substantially matches the shape of bills 203 and 205, which may be in one of the shapes shown in FIGS. 2B-2D or may be in another shape, and may have a uniform width or diameter when in an un-stretched or unexpanded state. In other embodiments, the insertable sleeve 501 may comprise a different natural shape than the shape of the bills 203 and 205 (e.g., an accordion shape, a fluted shape, a webbed shape, etc.), and may have a non-uniform width or diameter when in an un-stretched or unexpanded state.

As shown in FIG. 6A, the insertable sleeve 501 may further include one or more petals, such as petal 520, and a pull tab 522 positioned on the proximal opening 504 of the insertable sleeve 501. Petal 520 may, for example, assist the user with positioning the insertable sleeve 501 on the applicator 503, assist the user with positioning a speculum within the insertable sleeve 501 once the insertable sleeve 501 is deployed within the vagina of a patient, help the insertable sleeve 501 conform and fit more closely to the speculum, and so on. In the embodiment of FIG. 6A, the petal 520 further includes a perforated edge 524 on the body of the petal 520. The perforated edge may allow the petal 520 to be formed into a pocket (optionally, with the use of pull tab 522) that may be tucked over a top edge of an inserted speculum to secure the insertable sleeve 501 to the speculum, as will be described herein with respect to FIGS. 10A and 10B.

As with applicators 303 and 403, applicator 503 may assist the user with inserting and positioning the insertable sleeve 501 in the vagina of the patient. As shown in FIG. 6A, applicator 503 consists of more than one piece, a hollow plunger sheath 503*a* and a plunger 503*b* generally similar to the plunger 303*b* and 403*b* discussed above. The plunger sheath 503*a* fits inside the hollow sleeve channel of the insertable sleeve 501, and the plunger 503*b* fits inside the plunger sheath 503*a*. The distal end of the plunger sheath 503*a* may have one or more slits or openings 505 which are configured to capture a tucked end of the insertable sleeve 501 thereby securing the insertable sleeve 501 to the plunger sheath 503*a*. In this way or by another mechanism, insertable sleeve 501, the plunger sheath 503*a*, and the plunger 503*b* may be coupled together, with the plunger 503*b* inserted into the hollow plunger sheath 503*a* and the plunger sheath 503*a* inserted into the hollow sleeve channel of the insertable sleeve 501. However, in other embodiments, the applicator 503 may consist of one piece (e.g., a sleeve tube similar to sleeve tube 303*a*, a sleeve tube with flanges similar to applicator 403, etc.), or may consist of a different combination of pieces (e.g., similar to applicator 303 including sleeve tube 303*a* and plunger 303*b*).

Referring to the plunger-and-sheath embodiment of the applicator 503 shown in FIG. 6A, the plunger sheath 503*a* may include an elongated, cylindrical body with at least one open end at a proximal end 508 of the sheath 503*a* (i.e., the end designed to point out of the patient's vagina). A distal end 509 of the sheath 503*a* (i.e., the end designed to point into the patient's vagina) may, in various embodiments, be open, openable (e.g., similar to the distal end 409 of applicator 403), or closed. As shown in FIG. 6A, the plunger sheath 503*a* has a circular cylindrical body, but in other embodiments the cylindrical sleeve body may instead have a cross-sectional shape that is a triangle, a square, a rectangle, a hexagon, a circle, an oval, and so on. The plunger sheath 503*a* may further be flared at the proximal end 508 of the sheath 503*a*, for example, to allow the sheath 503*a* to more easily receive the plunger 503*b*. The distal end of the plunger 503*b* may also include a feature to limit insertion of the plunger or otherwise indicate that the plunger has been pushed into the plunger sheath 503*a* an appropriate amount to deploy the insertable sleeve 501. In some embodiment, this feature generates a click sound when the plunger reaches the proper position, indicating proper and/or full deployment of the sleeve.

The plunger sheath 503*a* may be designed to fit the shape of the inner surface of the insertable sleeve 501 (i.e., the hollow sleeve channel of sleeve 501) and/or to fit the shape of the plunger 503*b*. For example, the sheath 503*a* embodied in FIG. 6A is circular in shape to fit inside the circular sleeve body of the insertable sleeve 501, as well as to fit over a circular body of the plunger 503*b*. In other embodiments, however, the sheath 503*a* may take on a different shape from the insertable sleeve 501 and/or the plunger 503*b*. The plunger sheath 503*a* may be configured to be inserted into the hollow sleeve channel of the insertable sleeve 501 by any of the open ends of the insertable sleeve 501 (i.e., by the proximal opening 504 of the insertable sleeve 501 embodied in FIG. 6A). Additionally, the sheath 503*a* may be fully contained within the hollow sleeve channel of the insertable sleeve 501, may be of approximately the same length as the insertable sleeve 501, or may extend past the proximal opening 504 of the insertable sleeve 501.

The plunger 503*b* of the applicator 503 may include an elongated, cylindrical body configured to fit inside the plunger sheath 503*a*. As shown in FIG. 6A, the plunger 503*b* has a circular cylindrical body, though in other embodiments the cylindrical body of the plunger 503*b* may instead have a cross-sectional shape that is a triangle, a square, a rectangle, a hexagon, a circle, an oval, and so on. The body of the plunger 503*b* may be designed to fit the shape of the inner surface of the plunger sheath 503*a*. For example, the plunger 503*b* embodied in FIG. 6A has a circular cylindrical body to fit inside the hollow, circular cylindrical body of the plunger sheath 503*a*. In other embodiments, however, the plunger 503*a* may take on a different shape from the plunger sheath 503*a*. In some embodiments, the plunger 503*b* may further include a flared end (e.g., an end that distends outward from the cylindrical body of the sheath 503*a*), shown in FIG. 6A as flared end 510. Similar to flared end 310 of plunger 303*b*, the flared end 510 may be beneficial to a user by providing the user with a larger area by which to apply a force to the plunger 503*b* in order to release the insertable sleeve 501 from the applicator 503. The plunger 503*b* may be solid throughout the cylindrical body, or the plunger 503*b* may be hollow. In general, the applicator 503 provides the same benefits as those discussed with respect to applicator 303 above, such as ensuring limited contact with an outer surface of the insertable sleeve 501 during handling and insertion into the patient's vagina so that the insertable sleeve 501 remains sanitary.

FIG. 6A illustrates the insertable sleeve 501 in the process of being deployed by the applicator 503. Similar to insertable sleeve 301 with applicator 303, and insertable sleeve 401 with applicator 403, the insertable sleeve carried by applicator 503 can be inserted into a vagina of a patient, by the patient herself or by a practitioner, in a similar fashion to a tampon. To insert the insertable sleeve 501, the user, who may be a patient or a medical practitioner, holds the flared proximal end 508 of the plunger sheath 503*a* while pushing the plunger sheath 503*a* into the patient's vagina, with a distal end of the insertable sleeve 501 and a distal end of the plunger sheath 503*a* facing inward to the vagina. Because the plunger sheath 503*a* is coupled to the insertable sleeve 501 and the plunger 503*b*, pushing the sheath 503*a* into the patient's vagina also pushes the insertable sleeve 501 and the plunger 503*b* into the patient's vagina. The user continues to push the sheath 503*a* into the patient's vagina until the sheath 503*a* and the insertable sleeve 501 have reached a desired position within the vaginal cavity. In the embodiment shown in FIG. 6A, a desired position may be one in which the cylindrical sleeve body of the insertable sleeve 501 is completely or mostly in the patient's vagina, while the petal 520 remains outside of the vagina. Once the sheath 503*a* and the insertable sleeve 501 have reached the desired position, the user pushes or otherwise deploys the insertable sleeve 501 into the patient's vagina by, for example, applying a force to the plunger 503*b*.

The plunger 503*b* may be configured to work with the plunger sheath 503*a* in a variety of ways in order to release the insertable sleeve 501 positioned on the plunger sheath 503*a* into the patient's vagina. In one embodiment, the distal end of the plunger sheath 503*a* may be an open end. As such, when the user applies a force to the plunger 503*b* that is parallel to the plunger 503*b*, a distal end of the plunger 503*b* may move out of hollow cylindrical body of the plunger sheath 503*a* and come in contact with the distal end of the insertable sleeve 501. In this way, by continuing to push the plunger 503*b*, the user may push the insertable sleeve 501 off of the plunger sheath 503*a* and further into the patient's vagina, allowing for easy subsequent extraction of the applicator 503 from within the insertable sleeve 501.

In another embodiment, the distal end of the plunger sheath 503*a* may be openable (e.g., similar to the openable distal end 409 of applicator 403). When the user applies a force to the plunger 503*b* that is parallel to the plunger 503*b*, the distal end of the plunger 503*b* may come in contact with the openable distal end of the plunger sheath 503*b* and cause the distal end of the plunger sheath 503*b* to open. By continuing to apply a force to the plunger 503*b*, the user may cause the distal end of the plunger 503*b* to come in contact with the distal end of the insertable sleeve 501. In this way, by continuing to push the plunger 503*b*, the user may push the insertable sleeve 501 off of the plunger sheath 503*a* and further into the patient's vagina, allowing for easy subsequent extraction of the applicator 503 from within the insertable sleeve 501.

In yet another embodiment, the plunger sheath 503*a* may have a closed distal end and be configured to be expandable along the length of the sheath 503*a*. As such, applying a force to the plunger 503*b* that is parallel to the plunger 503*b* may cause the distal end of the plunger 503*b* to come in contact with the distal end of the sheath 503*a*, and continuing to apply a force to the plunger 503*b* may cause the sheath 503*a* to expand. The expansion of the sheath 503*a* may, in turn, push the insertable sleeve 501 further into the patient's vagina. This form of deployment may also allow the applicator 503 to be easily extracted because, for example, friction between the vaginal walls and the insertable sleeve 501 and/or a pressure on the insertable sleeve 501 caused by the vaginal walls prevents the insertable sleeve 501 from moving while the applicator 503 is extracted from the insertable sleeve 501. In other embodiments of the applicator 503, the applicator 503 may include a different release mechanism that releases, ejects, disengages, or otherwise causes the separation of the insertable sleeve 501 from the applicator 503.

Figure 6B:
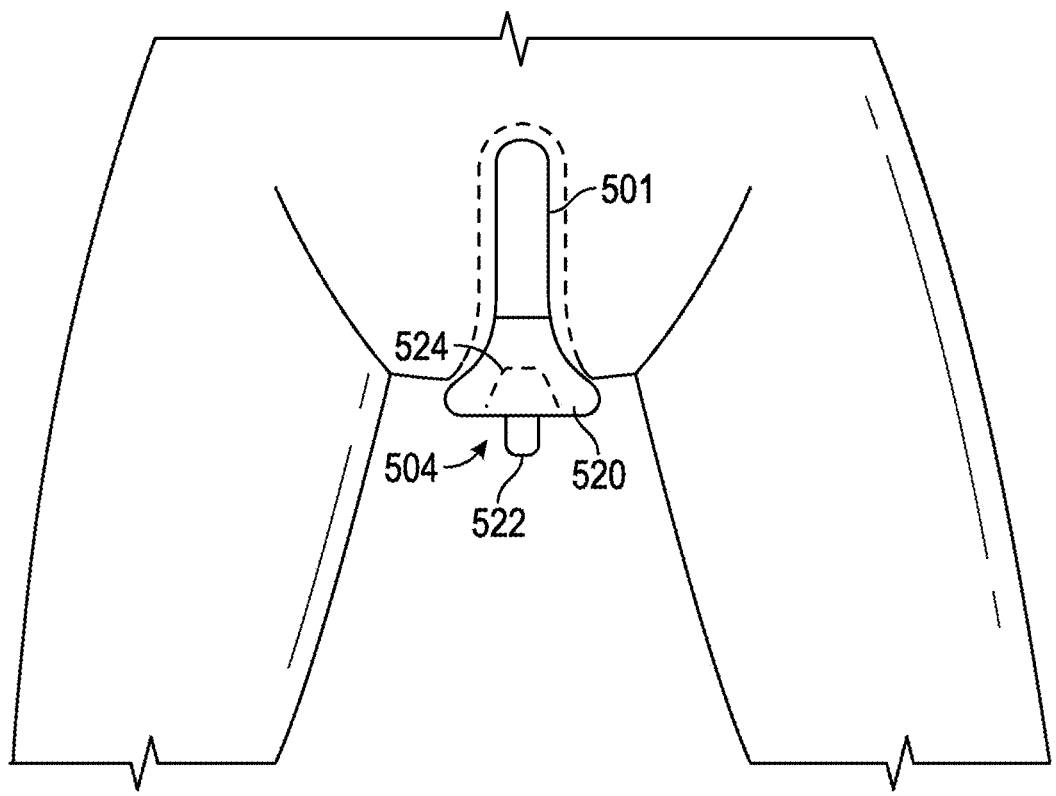
FIG. 6B is a front view of the insertable sleeve accessory of FIG. 6A having been inserted into the vagina of a patient.

As shown in FIG. 6B, once the insertable sleeve 601 has been positioned and released into the patient's vaginal cavity 400, the applicator 503 is removed from the patient's vagina, leaving the insertable sleeve 501 deployed in the patient's vagina. As illustrated in FIG. 6B, the insertable sleeve 601 is configured such that, when correctly positioned within the vaginal cavity 400, the petal 520 and the tab 522 should remain outside of the vaginal cavity 400. The applicator 503 may be disposable after it has delivered the insertable sleeve 501. Alternatively, one or more components of the applicator 503 (e.g., plunger sheath 503*a* and/or plunger 503*b*) may be reused after, e.g., sterilization.

The insertable sleeve 501, including the petal 520 and the pull tab 522, may be made of any of the materials described above with respect to sleeve 301, and the applicator 503 may be made of any of the materials described above with respect to applicator 303. As with insertable sleeve 301 and applicator 303, the insertable sleeve 501 and/or the applicator 503 may be coated with one or more bioactive or therapeutic agents, lubricants, powders, and/or surface finishes on inner and/or outer surfaces of the insertable sleeve 501 and the applicator 503. These lubricants, powders, and/or surface textures may work, for example, to help the insertable sleeve 501 more easily slide into the vagina of a patient, be more easily deployed within the vagina of the patient, be more easily decoupled from the applicator 503, and so on. Additionally, similar to insertable sleeve 501 and applicator 503, the insertable sleeve 501 and/or the applicator 503 may include ribbed details, texture differences, and/or gripping elements positioned on their inner and/or outer surfaces, for example, to help the applicator 503 remain coupled to the insertable sleeve 501 during insertion into the patient's vagina, help the insertable sleeve 501 grip a speculum inserted into a deployed insertable sleeve 501, and so on. Moreover, the insertable sleeve 501 may include one or more ridged finishes around the openings of insertable sleeve 501 (e.g., similar to the end rings 312 of insertable sleeve 301 shown in FIGS. 4A and 4B, similar to the end ring 412 of insertable sleeve 401 shown in FIGS. 5A and 5B, etc.), as described above with respect to insertable sleeve 301.

Figure 7A:
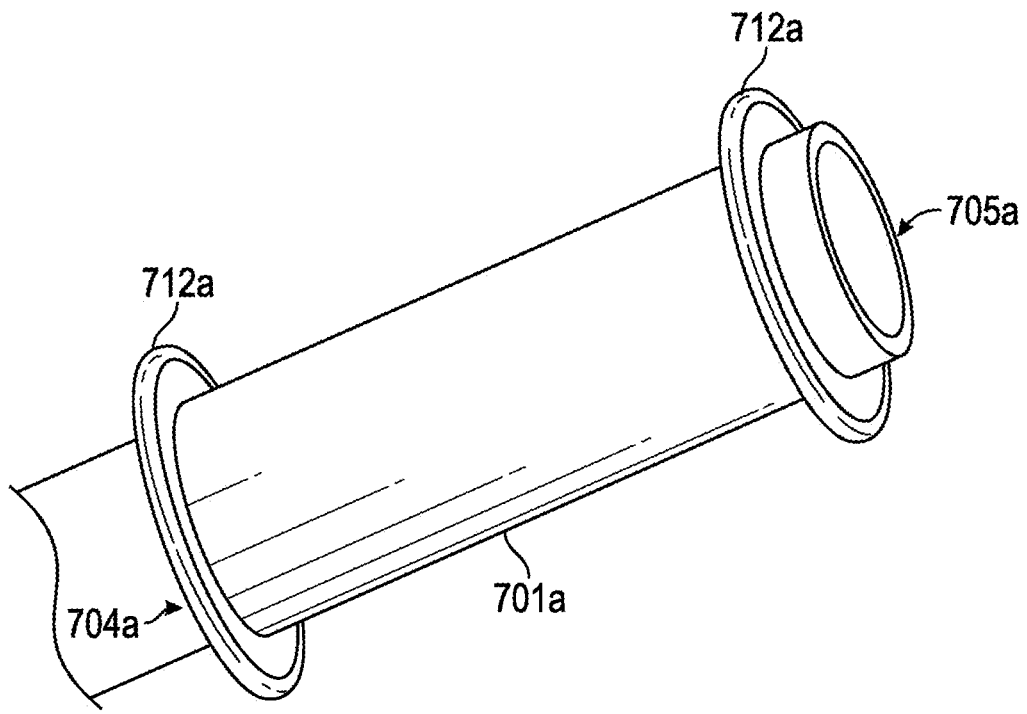
FIGS. 7A-7C depict various embodiments of an insertable sleeve accessory.
Figure 7B:
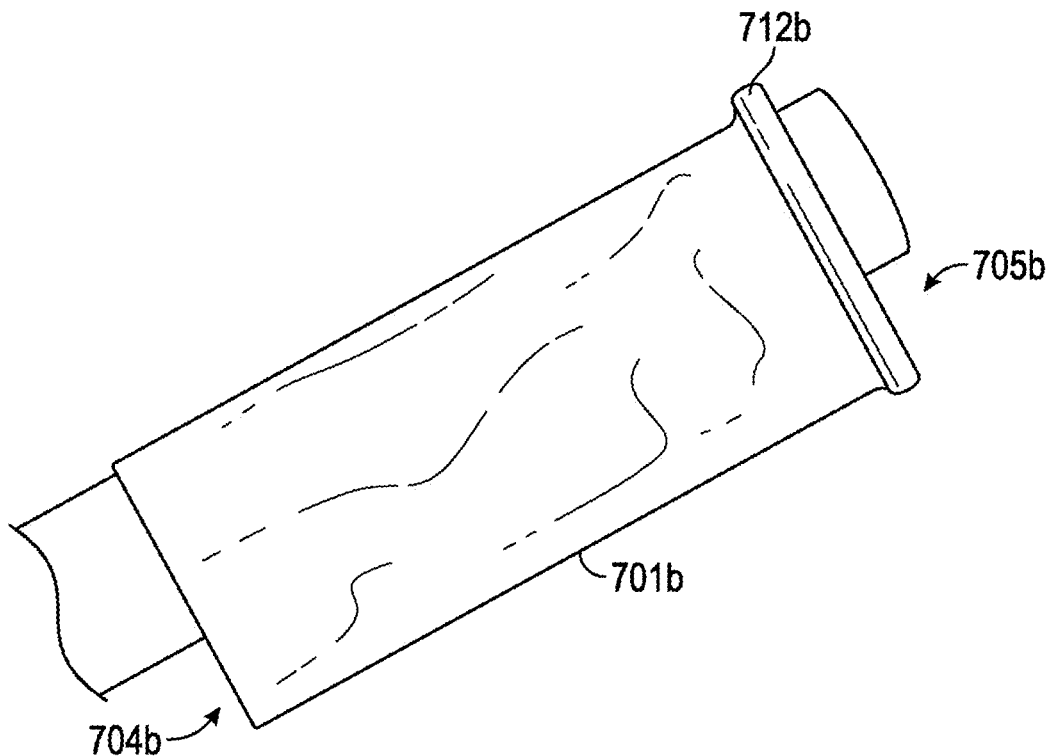
Figure 7C:
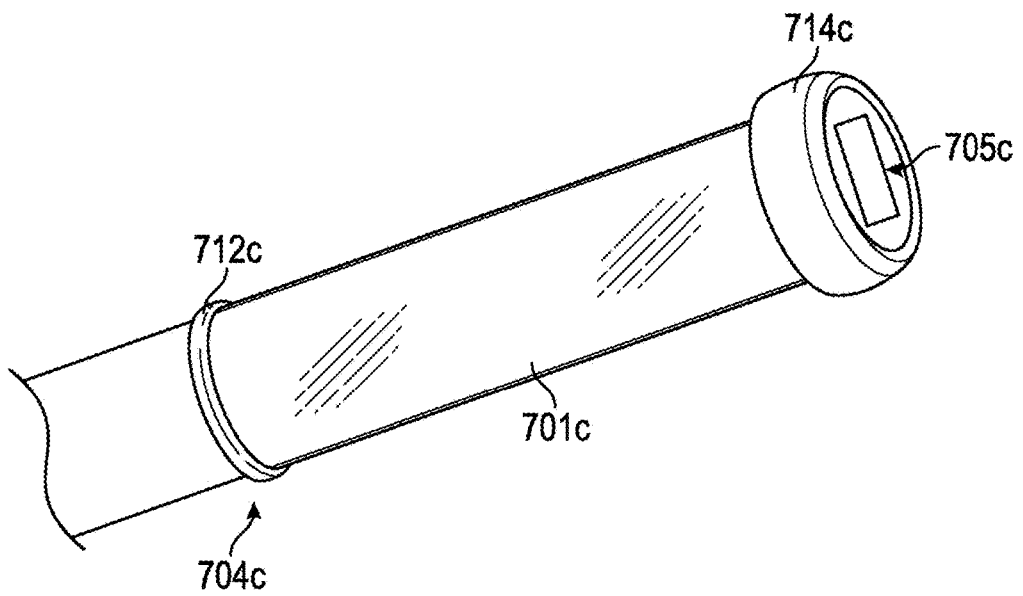

FIGS. 7A-7C depict alternative embodiments of an insertable sleeve accessory. The insertable sleeve accessories shown in FIGS. 7A-7C may be made of any of the materials described above with respect to sleeve 301. As with insertable sleeve 301, the insertable sleeve accessories may also be coated with one or more bioactive or therapeutic agents, lubricants, powders, and/or surface finishes on their inner and/or outer surfaces. Moreover, similar to insertable sleeve 301, the insertable sleeve accessories may include ribbed details, texture differences, and/or gripping elements positioned on their inner and/or outer surfaces.

The insertable sleeve accessories shown in FIGS. 7A-7C generally have cylindrical sleeve bodies, with inner walls or surfaces defining hollow areas (i.e., hollow sleeve channels) and outer walls or surfaces. The embodiments shown have circular cylindrical bodies, though other embodiments may instead have a cylindrical body with a cross-sectional shape that is a triangle, a square, a rectangle, a hexagon, a circle, an oval, and so on. The insertable sleeve accessories may be configured to receive an insertion portion of a speculum, such as insertion portion 211 of speculum 200, though proximal and/or distal openings in their cylindrical sleeve bodies. The insertable sleeve accessories shown in FIGS. 7A-7C may have uniform widths or diameters between proximal and distal ends, ranging between 0.25 and 4.0 inches when in an un-stretched or unexpanded state. Alternatively, the insertable sleeve accessories may have non-uniform widths or diameters, ranging between 0.25 and 4.0 inches when in an un-stretched or unexpanded state.

FIG. 7A illustrates an embodiment of an insertable sleeve accessory, shown as insertable sleeve accessory 701*a*. The cylindrical body of insertable sleeve 701*a* includes two openings, a proximal opening 704*a* and a distal opening 705*a*. As shown in FIG. 7A, the proximal opening 704*a* and the distal opening 705*a* are each lined with a ridged finish, shown as end rings 712*a*. The end rings 712*a* may provide any of the benefits discussed above with respect to end rings 312 of insertable sleeve 301. Importantly, the end ring 712*a* at the proximal opening 704*a* may help keep the proximal end 704*a* of the insertable sleeve 701*a* open after the insertable sleeve 701*a* has been released in a vaginal cavity, so that the insertable sleeve 701*a* may more easily receive an insertion portion of a speculum. Additionally, the end ring 712*a* at the distal opening 705*a* may help retain the insertable sleeve 701*a* in the desired position in the patient's vagina once deployed (by expanding into the vaginal fornices after insertion, similar to a female condom), help open the vaginal cavity for the obstetric or gynecological procedure being performed, help keep the insertable sleeve 701*a* on an applicator during insertion of the insertable sleeve 701*a* and applicator into the patient's vaginal cavity, and so on. In various embodiments, the end rings 712*a* may be provided as a rolled bead edge, formed from an encapsulated ring that is cured into the insertable sleeve 701*a*, and so on.

FIG. 7B illustrates an embodiment of an insertable sleeve accessory, shown as insertable sleeve accessory 701*b*. The cylindrical body of insertable sleeve 701*b* includes two openings, a proximal opening 704*b* and a distal opening 705*b*. As shown in FIG. 7A, distal opening 705*b* is lined with a ridged finish, shown as end ring 712*b*, while the proximal opening 704*b* remains unfinished. The end ring 712*b* may provide any of the benefits discussed above with respect to end rings 312 of insertable sleeve 301. the end ring 712*a* at the distal opening 705*a* may help retain the insertable sleeve 701*a* in the desired position in the patient's vagina once deployed, help open the vaginal cavity for the obstetric or gynecological procedure being performed, help keep the insertable sleeve 701*a* on an applicator during insertion of the insertable sleeve 701*a* and applicator into the patient's vaginal cavity, and so on. In various embodiments, the end ring 712*b* may be provided as a rolled bead edge, formed from an encapsulated ring that is cured into the insertable sleeve 701*b*, and so on. The end ring 712*b* may alternatively be provided as a ring, such as a rubber ring, that is rolled into the sleeve body of the insertable sleeve 701*b*, e.g., to prevent the sleeve body from sliding off an applicator while the applicator, coupled to the insertable sleeve 701*b*, is being inserted into the body of the patient.

FIG. 7C illustrates an embodiment of an insertable sleeve accessory, shown as insertable sleeve accessory 701*c*. The cylindrical body of insertable sleeve 701*c* includes two openings, a proximal opening 704*c* and a distal opening 705*c*. As shown in FIG. 7C, the proximal opening 704*c* is lined with a ridged finish, shown as end ring 712*c*, and the distal opening 705*c* is lined with a compressed finish, shown as foam ring 714*c*. The end ring 712*c* may provide any of the benefits discussed above with respect to end rings 312 of insertable sleeve 301. Importantly, the end ring 712*c* at the proximal opening of 704*c* may help keep the proximal end 704*c* of the insertable sleeve 701 open after the insertable sleeve 701 has been inserted into a patient's vaginal cavity, so that the insertable sleeve 701*c* may receive an insertion portion of a speculum. In various embodiments, the end ring 712*c* may be provided as a rolled bead edge, formed from an encapsulated ring that is cured into the insertable sleeve 701*c*, provided as a rubber ring that is rolled into the sleeve body, and so on.

A compressed finish, such as foam ring 714*c*, may be comprised of a foam or sponge ring of material that is attached to the sleeve body of an insertion sleeve. For example, foam ring 714*c* may be attached at the distal opening 709*c* of the insertable sleeve 701*c* by rolling the material of the distal opening 709*c* over the foam ring 714*c* and curing the material of the insertable sleeve 701*c*. The foam ring 714*c* may be compressed at insertion but may expand once in the vagina. Thus, the foam ring 714*c* may provide benefits of helping to retain the insertable sleeve 701*c* in position in the patient's vagina once deployed (by expanding into the vaginal fornices after insertion, similar to a female condom), help open the vaginal cavity for the obstetric or gynecological procedure being performed, etc., while allowing for easy insertion into the vaginal cavity of the patient while in the compressed form.

Figure 8A:
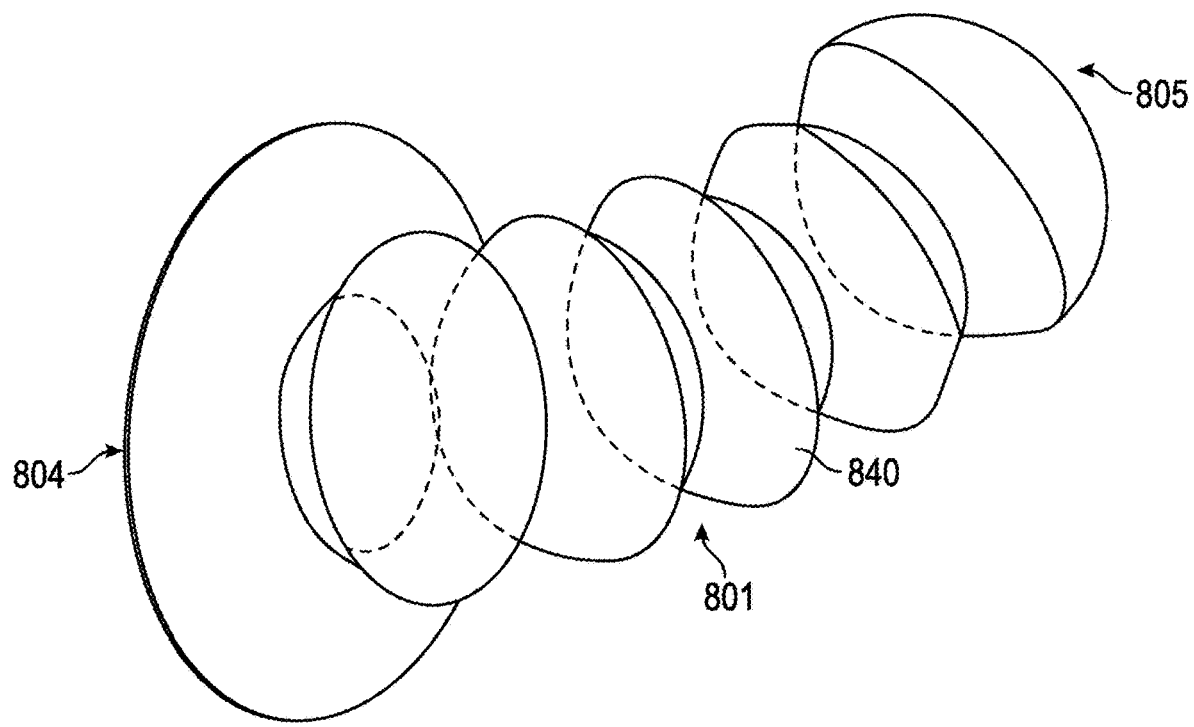
FIGS. 8A-8O depict various exemplary embodiments of an insertable sleeve accessory.
Figure 8B:
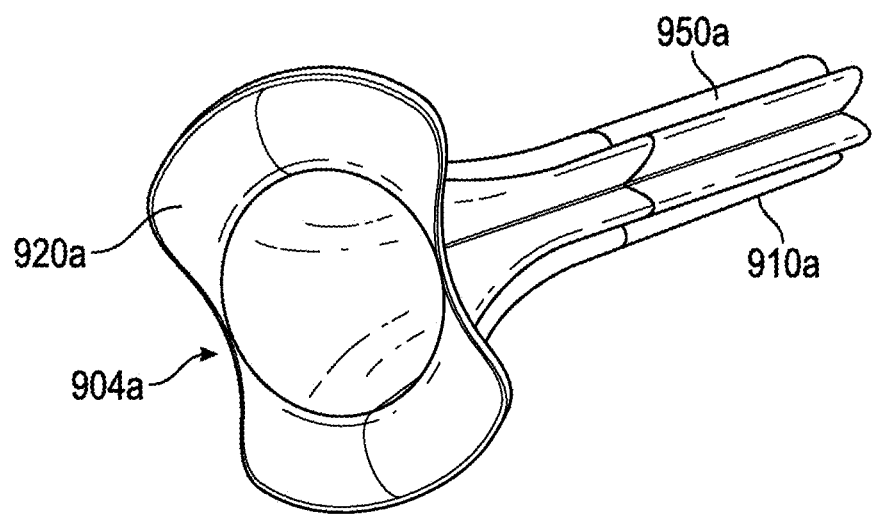
Figure 8C:
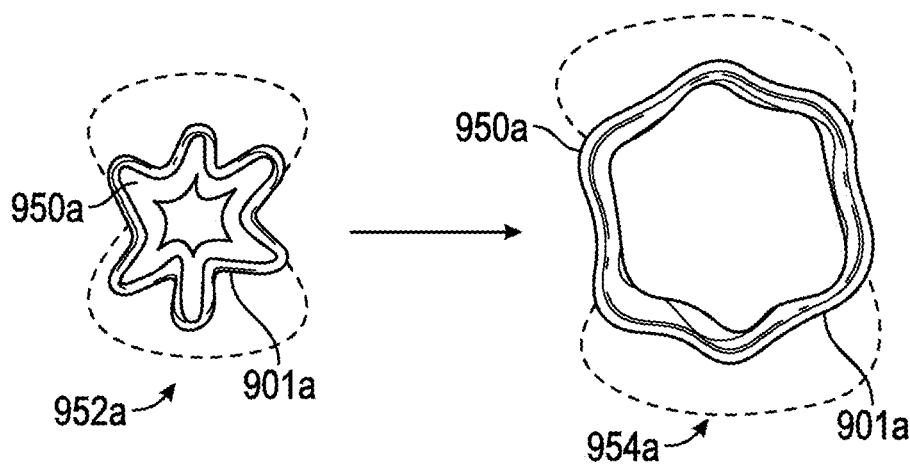
Figure 8G:
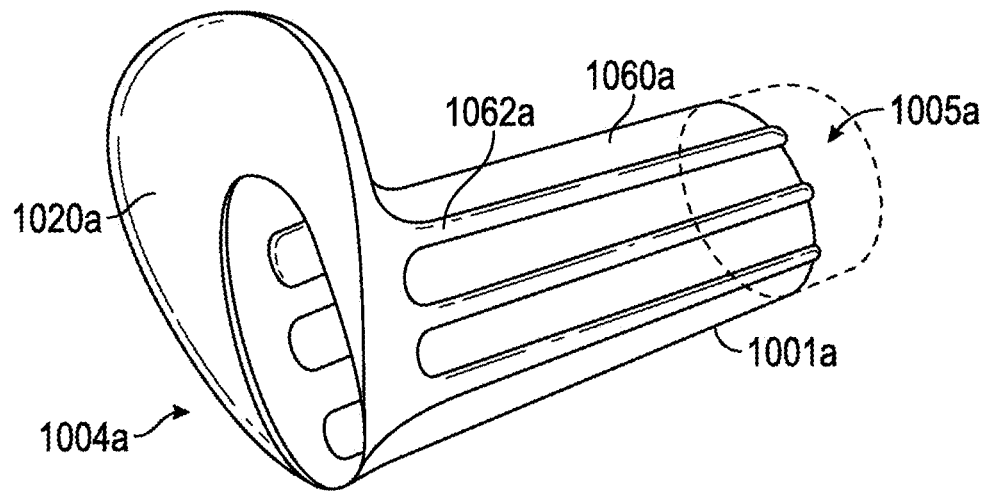
Figure 8H:
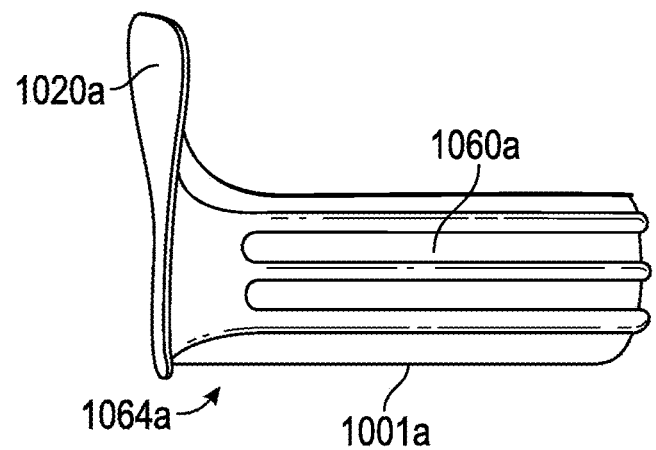
Figure 8H:
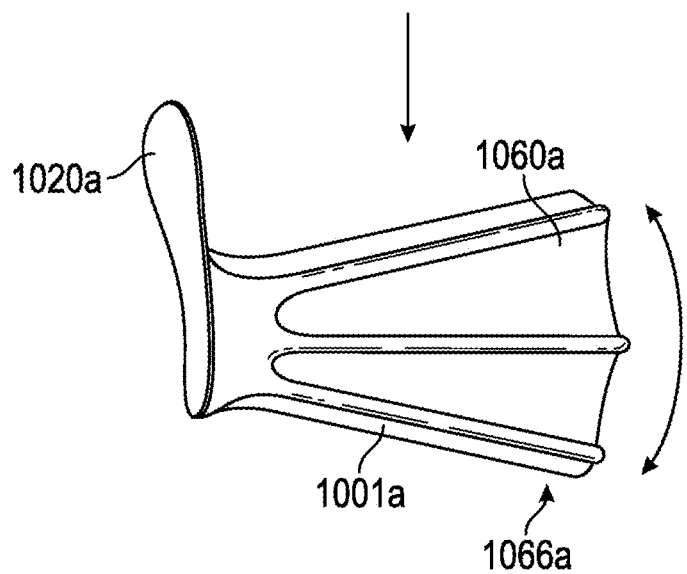
Figure 8I:
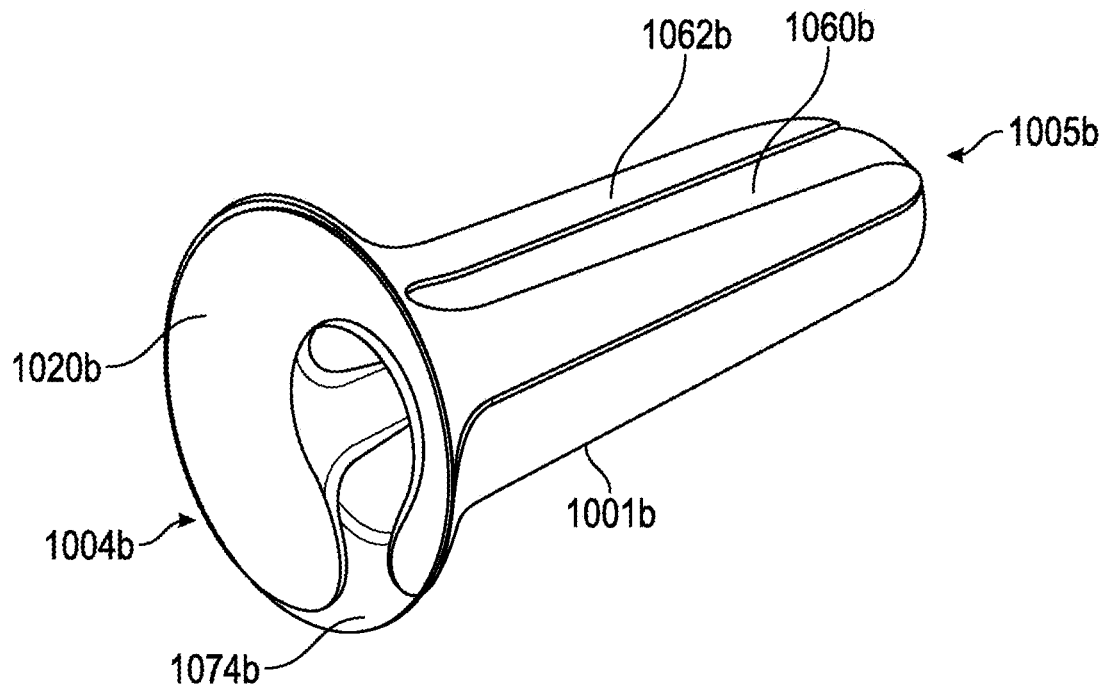
Figure 8J:
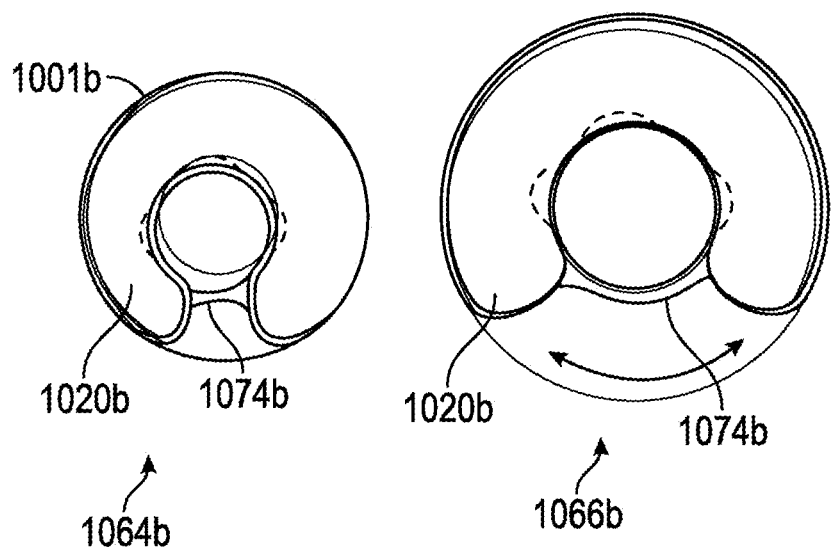
Figure 8N:
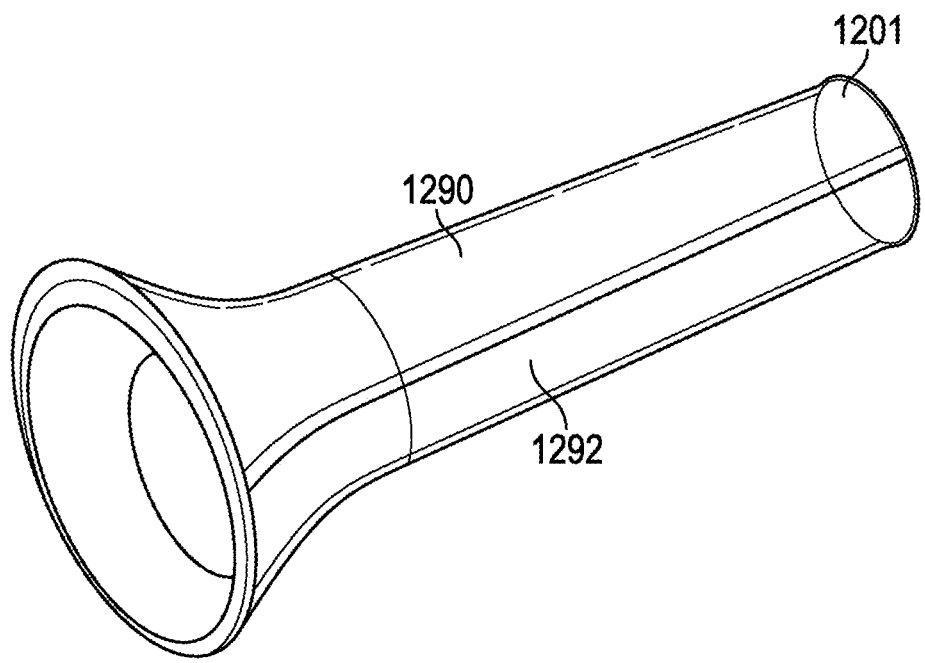
Figure 8O:
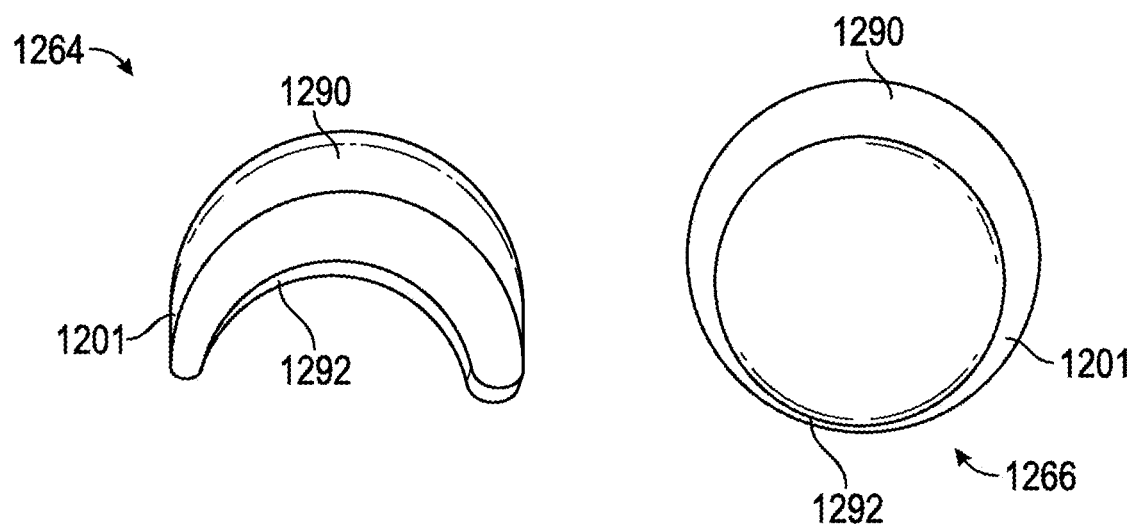

FIGS. 8A-8O depict additional alternative embodiments of an insertable sleeve accessory. The insertable sleeve accessories shown in FIGS. 8A-8O may be made of any of the materials described above with respect to sleeve 301, for example, poly materials such as polypropylene, polyurethane, silicone, etc. or a combination thereof. As with insertable sleeve 301, the insertable sleeve accessories may also be coated with one or more bioactive or therapeutic agents, lubricants, powders, and/or surface finishes on their inner and/or outer surfaces. Moreover, similar to insertable sleeve 301, the insertable sleeve accessories may include ribbed details, texture differences, and/or gripping elements positioned on their inner and/or outer surfaces.

The insertable sleeve accessories shown in FIGS. 8A-8O generally have cylindrical sleeve bodies, with inner walls or surfaces defining hollow areas (i.e., hollow sleeve channels) and outer walls or surfaces. The embodiments shown generally have circular cylindrical bodies, though other embodiments may instead have a cylindrical body with a cross-sectional shape that is a triangle, a square, a rectangle, a hexagon, a circle, an oval, and so on. The insertable sleeve accessories may be configured to receive an insertion portion of a speculum, such as insertion portion 211 of speculum 200, through proximal and/or distal openings in their cylindrical sleeve bodies. These openings in the cylindrical sleeve bodies of the insertable sleeve accessories shown in FIGS. 8A-8O may further be edged in ridged and/or compressed finishes, similar to end rings 312 shown in FIGS. 4A and 4B and/or foam ring 714*c* shown in FIG. 7C. In various embodiments, the insertable sleeve accessories may have widths or diameters that vary between 0.25 and 4.0 inches.

FIG. 8A illustrates an embodiment of an insertable sleeve accessory, shown as insertable sleeve accessory 801. Insertable sleeve 801 includes a plurality of folds 840 throughout the cylindrical sleeve body of insertable sleeve 801, such that insertable sleeve 801 is configured to fold and unfold similarly to an accordion. In this way, insertable sleeve 801 may be easily compressed to a much smaller width than other embodiments of insertable sleeve accessories that would have to be rolled or carefully folded in order to be compressed. In some embodiments, insertable sleeve 801 may be stored or packaged in the compressed, accordion form, e.g., in an individual container designed to accommodate the compressed, accordion form of insertable sleeve 801. In the embodiment of FIG. 8A, insertable sleeve 801 has an open proximal end 804 and an open distal end 805. In other embodiments of insertable sleeve 801, the insertable sleeve 801 may have a closed distal end that is a dissolvable end, or a closed distal end including a narrow opening configured to catch the distal end of an applicator and thereby allow easy insertion of the insertable sleeve 801 into the vagina of a patient. In some embodiments, the narrowest portions of the folds 840 may range down to 0.25 inches and the widest portions of the folds 840 may range up to 4.0 inches when the insertable sleeve 801 is in an un-stretched or unexpanded state.

FIGS. 8B-8C illustrate an embodiment of an insertable sleeve accessory, shown as insertable sleeve accessory 901*a*. Insertable sleeve 901*a* includes a plurality of flutes 950*a* formed lengthwise into the cylindrical sleeve body of the insertable sleeve 901*a*. As shown in FIG. 8C, the flutes 950*a* may allow the insertable sleeve 901*a* to be compressed down, similar to an accordion, in the widthwise direction of insertable sleeve 901*a* (i.e., into compressed form 952*a*). Later, the insertable sleeve 901*a* may expand into a configuration with a much larger diameter (i.e., into opened form 954*a*). For example, the insertable sleeve 901*a* may be inserted into a patient's vagina in the compressed form 952*a* and may be expanded into the opened form 954*a* by inserting a speculum into the insertable sleeve 901*a*. Additionally, the flutes 950*a* may even provide the insertable sleeve 901*a* with enough rigidity that the insertable sleeve 901*a* may be inserted into the vagina of a patient without the use of an applicator. In some embodiments, insertable sleeve 901*a* may be stored or packaged in the compressed form 952*a*, e.g., in individual containers designed to accommodate the compressed form 952*a* of insertable sleeve 901*a*.

Referring back to FIG. 8B, insertable sleeve 901a may also include one or more petals, such as petal 920a, at a proximal opening 904a of the insertable sleeve 901a. Petal 920a may be configured similarly to petal 520 discussed above with respect to FIGS. 6A and 6B. For example, petal 920a may configured such that, when the insertable sleeve 901a is inserted into the patient's vagina, the petal 920a remains outside of the vagina, e.g., to assist a user with inserting a speculum into the insertable sleeve 901a positioned in the vagina. In some embodiments, the petal 920a may further include a perforated edge, similar to perforated edge 524 of petal 520 discussed above with respect to FIGS. 6A and 6B, on the body of the petal 920a. The perforated edge may allow the petal 920a to be formed into a pocket that may be tucked over a top edge of an inserted speculum to secure the insertable sleeve 901a to the speculum, as will be described herein with respect to FIGS. 10A and 10B.

FIGS. 8D-8F illustrate an alternative embodiment of a fluted insertable sleeve accessory, shown as insertable sleeve accessory 901b. As with insertable sleeve 901a, insertable sleeve 901b includes a plurality of flutes 950b formed lengthwise into the cylindrical sleeve body of the insertable sleeve 901b. As shown in FIG. 8E, the flutes 950b may allow the insertable sleeve 901b to be compressed down into compressed form 952b, and later the insertable sleeve 901b may expand into an opened form 954b with a much larger diameter. For example, the insertable sleeve 901b may be inserted into a patient's vagina in the compressed form 952b and may be expanded into the opened form 954b by inserting a speculum into the insertable sleeve 901b. Additionally, the insertable sleeve 901b may be fluted in such a way (e.g., because the insertable sleeve 901b is fully injection molded) that the insertable sleeve 901b naturally contracts into the compressed form 952b. In some embodiments, insertable sleeve 901b may be stored or packaged in the compressed form 952b, e.g., in individual containers designed to accommodate the compressed form 952b of insertable sleeve 901b.

As shown in FIG. 8F, insertable sleeve accessory 901b may be configured to be inserted into the vaginal cavity of a patient through the use of an applicator 903b. Applicator 903b may include a hollow, cylindrical body with an open distal end and an open proximal end configured to receive the sleeve accessory 901b therein. The cylindrical body of applicator 903b may further include a ridged portion, shown as 906b. The applicator 903b may be configured to be inserted into the vaginal cavity of the patient up until the ridged portion 906b. The insertable sleeve accessory 901b may then be threaded through the hollow portion of the cylindrical body of the applicator 903b and thereby deployed into the patient's vaginal cavity.

FIGS. 8G-8H illustrate an embodiment of an insertable sleeve accessory, shown as insertable sleeve accessory 1001a. Insertable sleeve 1001a includes a plurality of webs 1060a formed between prongs 1062a, with both the webs 1060a and the prongs 1062a running lengthwise along the cylindrical sleeve body of the insertable sleeve 1001a between a proximal opening 1004a and a distal opening 1005a. As shown in FIG. 8H, the webs 1060a may allow the insertable sleeve 1001a to expand at the distal opening 1005a of the insertable sleeve 1001. For example, the webs 1060a may allow the un-stretched, generally circular cylindrical sleeve body of insertable sleeve 1001a (i.e., un-stretched form 1064a) to stretch at the distal opening 1005a to form a generally conical sleeve body shape (i.e., stretched form 1066a). In one embodiment, the insertable sleeve 1001a may be inserted into a patient's vagina in the un-stretched form 1064a and may be expanded into the stretched form 1066a by inserting a speculum into the insertable sleeve 1001a and opening the speculum. Additionally, in some embodiments, the prongs 1062a may even provide the insertable sleeve 1001a with enough rigidity that the insertable sleeve 1001a may be inserted into the vagina of a patient without the use of an applicator. In some embodiments, insertable sleeve 1001a may be stored or packaged in the un-stretched form 1064a, e.g., in an individual container designed to accommodate the un-stretched form 1064a of insertable sleeve 1001a.

As shown in FIG. 8G, insertable sleeve 1001a may also include one or more petals, shown as petal 1020a, at the proximal opening 1004a of the insertable sleeve 1001a. Petal 1020a may be configured similarly to petal 520 discussed above with respect to FIGS. 6A and 6B. For example, petal 1020a may configured such that, when the insertable sleeve 1001a is inserted into the patient's vagina, the petal 1020a remains outside of the vagina, e.g., to assist a user with inserting a speculum into the insertable sleeve 1001a positioned in the vagina. Alternatively, petal 1020a may be configured differently from petal 520. For example, the petal 1020 may be a flexible part that is injection-molded as one piece along with the prongs 1062. In some embodiments, the insertable sleeve 1001a may be formed as a single piece part, including the petal 1020a, the webs 1060a, and the prongs 1062a, and formed, e.g., from a thin, stretchy, clear silicone or be partially comprised of a semi-rigid injection molded part with a more flexible layer of polymer adhered or connected to it. In some embodiments, the petal 1020 may further include a perforated edge, similar to perforated edge 524 of petal 520 discussed above with respect to FIGS. 6A and 6B, on the body of the petal 1020. The perforated edge may allow the petal 1001a to be formed into a pocket that may be tucked over a top edge of an inserted speculum to secure the insertable sleeve 1001a to the speculum, as will be described herein with respect to FIGS. 10A and 10B.

FIGS. 8I-8J illustrate an alternative embodiment of a webbed sleeve accessory, shown as insertable sleeve accessory 1001b. As with insertable sleeve 1001a, insertable sleeve 1001b includes a plurality of webs 1060b formed between prongs 1062b, with both the webs 1060b and the prongs 1062b running lengthwise along the cylindrical sleeve body of the insertable sleeve 1001b between a proximal opening 1004b and a distal opening 1005b. Additionally, insertable sleeve 1001b may include a C-shaped petal 1020b at the proximal end 1004b with webbing 1074b formed between the two C-ends of the C-shaped petal 1020b. As shown in FIG. 8J, the webs 1060b and the webbing 1074b may allow the insertable sleeve 1001b to expand open from an un-stretched form 1064b to a stretched form 1066b with a larger diameter. In one embodiment, the insertable sleeve 1001b may be inserted into a patient's vagina in the un-stretched form 1064b and may be expanded into the stretched form 1066b by inserting a speculum into the insertable sleeve 1001b and/or opening the speculum inside the insertable sleeve 1001b. Additionally, in some embodiments, the prongs 1062b may even provide the insertable sleeve 1001b with enough rigidity that the insertable sleeve 1001b may be inserted into the vagina of a patient without the use of an applicator. In some embodiments, insertable sleeve 1001b may be injection molded or dip molded, or a combination of both. In some embodiments, insertable sleeve 1001b may also be stored or packaged in the un-stretched form 1064b, e.g., in an individual container designed to accommodate the un-stretched form 1064b of insertable sleeve 1001b.

FIGS. 8K-8M illustrate an embodiment of an insertable sleeve accessory, shown as insertable sleeve accessory 1101. As shown in FIG. 8K, insertable sleeve 1101 includes a plurality of structural bars (e.g., that may be injection molded), shown as ribs 1180, near a distal end 1105 of cylindrical body of the insertable sleeve 1101. Additionally, insertable sleeve 1101 may include a stiff tab 1182 (e.g., that may be injection molded) stretching along a length of the cylindrical body of the insertable sleeve 1101, from the proximal end 1105 and out of a distal end 1104.

In some embodiments, the ribs 1180 may add internal structure to an otherwise flexible cylindrical sleeve body (e.g., that may be injection molded or dip molded) of the insertable sleeve 1101, aiding in an initial insertion of the insertable sleeve 1101 into a vaginal cavity of a patient. As shown in FIG. 8L, the ribs 1180 may be spaced around a circumference of the flexible cylindrical sleeve body such that the sleeve body may contract down to a compressed form 1164 or expand to an opened form 1166 (e.g., when a speculum is inserted into the hollow sleeve channel of the insertable sleeve 1101). Referring back to FIG. 8K, the tab 1182, which may be stiffer than the other components of the insertable sleeve 1101, may serve as built-in applicator for the insertable sleeve 1101. For example, the user may push a remainder of the insertable sleeve 1101 into the vaginal cavity by applying a force through the tab 1182. Moreover, the tab 1182 may provide a user with a place to hold the insertable sleeve 1101 while inserting a speculum into the hollow sleeve channel of the insertable sleeve 1101.

As shown in FIG. 8M, insertable sleeve 1101 may, additionally or alternatively, be configured to be used with an applicator 1103. The applicator 1101 may be configured as a cone with a hole or aperture in the center, with the large-diameter end of the cone facing towards the proximal opening 1104 and the small-diameter end of the cone facing towards the distal opening 1105. The applicator may be configured to receive the cylindrical sleeve body of the insertable sleeve 1101 through the hole. For example, a user may insert the applicator into the vaginal cavity of the patient and thread the insertable sleeve 1101 through the hold of the applicator 1103 in order to deploy the insertable sleeve 1101 into the vaginal cavity.

FIGS. 8N-8O illustrate an embodiment of an insertable sleeve accessory, shown as insertable sleeve accessory 1201. A portion of insertable sleeve 1201 is thicker and more structural, shown in FIG. 8N as top half 1290, and a portion of insertable sleeve 1201 is thinner and collapsible, shown in FIG. 8N as bottom half 1292. The thicker, structural top half 1290 (e.g., that may be injection molded) is configured to provide rigidity to the insertable sleeve 1201, e.g., such that insertable sleeve 1201 may be inserted into a vaginal cavity of a patient without an applicator. The thinner, collapsible bottom half 1292 (e.g., that may be injection molded or dip molded) is configured to allow the insertable sleeve 1201 to collapse (e.g., fold up like a silicone menstrual cup), as well as stretch or expand to accommodate a speculum in the hollow sleeve channel of the insertable sleeve 1201. As shown in FIG. 8O, insertable sleeve 1201 may be collapsed into a compressed form 1264 by folding the bottom half 1292. In some embodiments, the insertable sleeve 1201 may be stored or packaged in the compressed form 1264, e.g., in an individual container designed to accommodate the compressed form 1264. However, insertable sleeve 1201 may also be stretched or expanded into an expanded form 1266 by stretching or expanding the bottom half 1292.

Any closed ends of insertable sleeve accessories described above, or otherwise envisioned, may be provided as a dissolvable cap. A dissolvable cap is a solid tip that dissolves once inserted into a patient's vagina, leaving an open tip. A dissolvable cap may be beneficial, for example, because it may allow an insertable sleeve accessory to be inserted into a vagina with a closed end, which may facilitate the use of an applicator with the insertable sleeve accessory. However, once in the vagina, the tip may dissolve, leaving an open end by which a practitioner may perform a medical procedure or examination.

Figure 9:
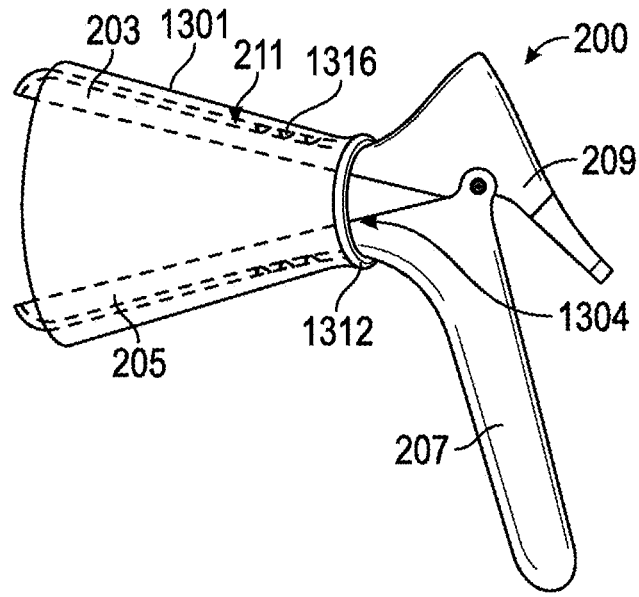
FIG. 9 is a side view of an embodiment of an insertable sleeve accessory positioned on a medical speculum, subsequent to the insertable sleeve accessory being positioned in the vagina of a patient.

As shown in FIG. 9, once an insertable sleeve accessory has been positioned in the patient's vagina (e.g., as shown in FIG. 4B, FIG. 5B, or FIG. 6B), the insertable sleeve accessory is configured to receive an elongated insertion portion of a speculum, such as insertion portion 211 of speculum 200. The insertable sleeve accessory of FIG. 9, shown as insertable sleeve accessory 1301 is configured similarly, for example, to insertable sleeve 401 discussed above with respect to FIGS. 5A and 5B. Insertable sleeve 1301 includes a cylindrical sleeve body configured to be slid over an insertion portion of a speculum, such as insertion portion 211 of the speculum 200, by a hollow sleeve channel defined by an inner surface of the cylindrical sleeve body. As discussed above with respect to, e.g., insertable sleeve 301, to facilitate the insertion of the speculum 200, the insertable sleeve accessory 1301 in some embodiments may be further configured to substantially match the shape of the bills 203 and 205 while the bills 203 and 205 are in the closed position. As shown in FIG. 9, the cylindrical body of insertable sleeve 1301 also has an open proximal end and an open distal end. In some embodiments, the sleeve 1301 may have a closed distal end, and may further include a small hole or aperture in the closed, distal end of the insertable sleeve 1301, which may allow for visualization, tissue sampling, etc. through the otherwise closed distal end.

When the bills 203 and 205 are in the closed position, the speculum 200 can be inserted into the insertable sleeve 1301 positioned in the patient's vagina. The user places the insertion portion 211 in line with an opening of the vagina and the proximal opening 1304 of the sleeve 1301 and applies a force parallel to the bills 203 and 205 to push the bills into the vagina. The sleeve 1301 may be made of a material that reduces the resistance between the sleeve 301 and the bills 203 and 205 of the speculum. Alternatively, or additionally, the sleeve 1301 may contain a lubrication (e.g., pre-applied) on its inner walls to facilitate entry and removal of the bills 203 and 205 of the speculum 200.

Figure 11:
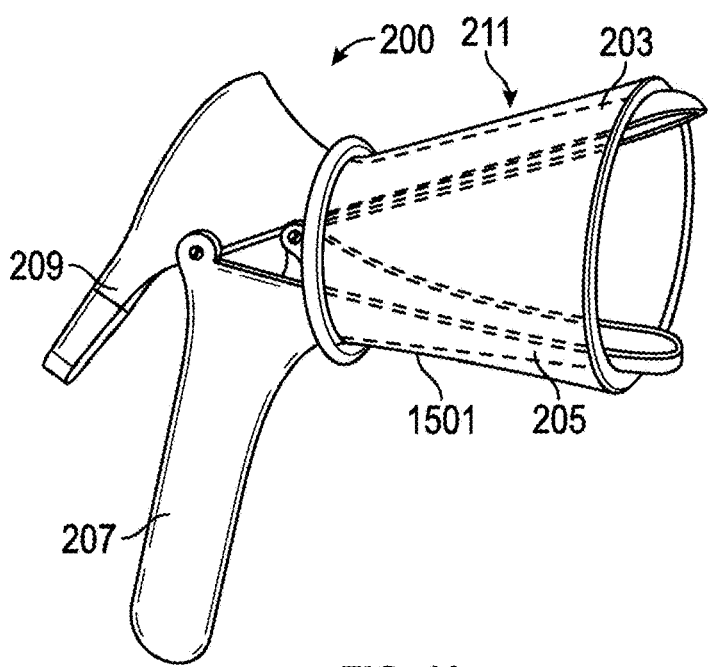
FIG. 11 is a side perspective view of an insertable sleeve accessory and a medical speculum in an open position.

The user may position the speculum 200 at a depth of the vagina to provide a clear view of the cervix when the bills 203 and 205 of the speculum are opened, as seen in FIGS. 9 and 11. As an example, the speculum 200 may be inserted so that the end of the bills 203 and 205 are located below the cervix. Once the bills 203 and 205 are separated, the cervix may then be seen through the viewing opening created by the separation of the bills 203 and 205.

Figure 10A:
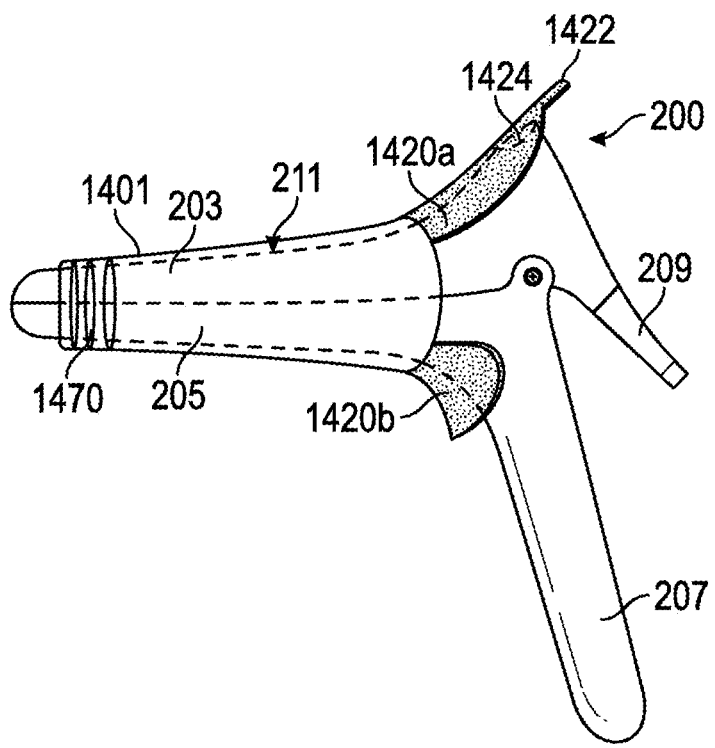
FIG. 10A is a side view of an embodiment of an insertable sleeve accessory positioned on a medical speculum.
Figure 10B:
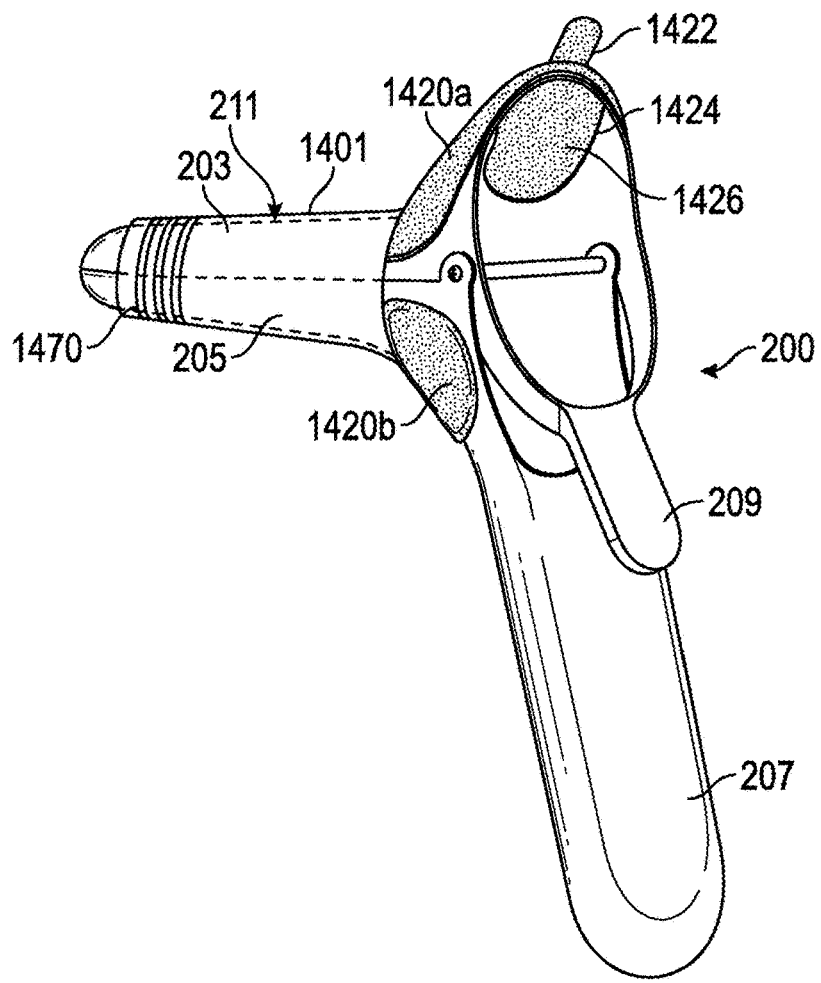
FIG. 10B is a rear perspective view of the insertable sleeve accessory of FIG. 10A positioned on a medical speculum.

In the embodiment shown in FIG. 9, the insertable sleeve 1301 may not reach the end of the bills 203 and 205 when the insertable sleeve 1301 is positioned on the bills 203 and 205 (e.g., similar to sleeve 1401 shown in FIGS. 10A and 10B). In some embodiments, the sleeve 1301 is positioned and dimensioned to cover at least 80% of the total length of the insertion portion 211. In other embodiments, the sleeve 1301 is positioned and dimensioned to cover at least 50% of the total length of the insertion portion 211. In some embodiments, the insertable sleeve 1301 extends from the proximal end of the bills 203 and 205 towards the distal end, but does not reach the distal end of the bills 203 and 205 (e.g., similar to sleeve 1401 shown in FIGS. 10A and 10B). In other embodiments, the insertable sleeve 1301 may extend from the distal end of the bills 203 and 205 towards the proximal end but not reach the proximal end of the bills 203 and 205.

In order to assist with capturing the insertable sleeve 1301 on the speculum 200, or prevent the insertable sleeve 1301 from sliding off the bills 203 and 205 during use and/or removal of the speculum 200, the insertable sleeve 1301 may include gripping elements, such as ridges, bumps, flanges, barbs, indentations, etc., on the interior of the insertable sleeve 1301 to increase the resistance between the insertable sleeve 1301 and the bills 203 and 205. In FIG. 9, the gripping elements are in the form of flanges 1316 extending inwardly from the interior of insertable sleeve 1301. The flanges 1316 may alternatively extend substantially perpendicular to the longitudinal axis of the insertable sleeve 1301, may extend at another angle, or may extend at a combination of angles. In a preferred embodiment, shown in FIG. 9, the flanges 1316 extend at an angle towards the distal end of the insertable sleeve 1301 and bills 203 and 205. In this way, the flanges 1316 are oriented in opposition to the direction of removal of the insertable sleeve 1301 from the speculum 200. Accordingly, small forces such as those that may act on the insertable sleeve 1301 during use with the speculum 200 or removal of the speculum 200 coupled to the insertable sleeve 1301 from the patient's vagina are likely not strong enough to overcome the resistance created by the flanges 1316. Other connection mechanisms for securing the insertable sleeve 1316 to the speculum 200 are intended to fall within the spirit and scope of the present disclosure, such as ribbed details and texture differences similar to those discussed above with respect to sleeve 301. The flanges 1316 or any other connection mechanisms could also be used in any of the sleeves described herein.

Additionally, as shown in FIG. 9, the open proximal end of insertable sleeve 1301 includes a ridged finish in the form of an end ring 1312. End ring 1312 is configured similarly to the end rings 312 discussed above with respect to FIGS. 4A and 4B. Moreover, similar to insertable sleeve 301, insertable sleeve 1301 may include lubricants, powders, surface textures, and so on, for example to aid the insertable sleeve 1301 in being slid onto the insertion portion 211 of the speculum 200. Insertable sleeve 1301 may be made of any of the materials described above with respect to insertable sleeve 301.

FIGS. 10A and 10B show another embodiment of an insertable sleeve accessory, shown as insertable sleeve accessory 1401, positioned on a speculum, such as speculum 200. The insertable sleeve accessory of FIGS. 10A and 10B is configured similarly, for example, to insertable sleeve accessory 501 discussed above with respect to FIGS. 6A and 6B. Insertable sleeve 1401 includes a cylindrical sleeve body configured to be slid over an insertion portion of a speculum, such as insertion portion 211 of the speculum 200, by a hollow sleeve channel defined by an inner surface of the cylindrical sleeve body. As discussed above with respect to, e.g., insertable sleeve 301, to facilitate the insertion of the speculum 200, the insertable sleeve accessory 1401 in some embodiments may be further configured to substantially match the shape of the bills 203 and 205 while the bills 203 and 205 are in the closed position. As shown in FIGS. 10A and 10B, the cylindrical body of insertable sleeve 1401 also includes openings at both ends (i.e., at the proximal sleeve body end and the distal sleeve body end), through other embodiments of insertable sleeve 1401 may include an opening at only one end of the cylindrical sleeve body.

Insertable sleeve 1401 also includes petals 1420a and 1420b, as well as pull tab 1422, positioned on the proximal end of the insertable sleeve 1401. The petals 1420a and 1420b may, for example, assist with positioning the sleeve 1401 on the speculum 200 and/or help the sleeve 1401 conform and fit more closely to the speculum 200 once positioned on the speculum 200. As shown in the embodiment of FIG. 10A, the petal 1420a further includes a perforated edge 1424 on the body of the petal 1420a. The body of the sleeve 1401 may be made of any of the materials described above with respect to sleeve 301. The petals 1420a and 1420b and the pull tab 1422 may be made of the same material(s) as the body of the insertable sleeve 1401, or the petals 1420a and 1420b may be made of one or more different materials from the insertable sleeve 1401. The petals and pull tab may all be separate pieces or alternatively be details in a singular piece.

FIG. 10A shows insertable sleeve 1401 positioned on the insertion portion 211 of the speculum 200. As shown in FIG. 10A, insertable sleeve 1401 includes ribbed details 1470 on the distal end of the sleeve 1401. The ribbed details 1470 may help the sleeve 1401 remain securely fastened onto the insertion portion 211. In other embodiments, insertable sleeve 1401 may include ribbed details, additionally or alternatively, on the proximal end of the sleeve 1401 or distributed along the length of the insertable sleeve 1401. In yet other embodiments, the sleeve 1401 may, additionally or alternatively, include texture differences and/or gripping elements (e.g., similar to flanges 1316 from sleeve 1301 shown in FIG. 9) on an inner surface of the sleeve 1401 to help the insertable sleeve 1401 remain securely fastened onto the insertion portion 211. Additionally, the sleeve 1401 may include bioactive or therapeutic agents, lubricants, powders, and/or surface textures applied to an inner surface and/or an outer surface of the sleeve 1401, as described above with respect to sleeve 301. The sleeve 1401 may further include a ridged finish (e.g., similar to end rings 312 of sleeve 301 shown in FIGS. 4A and 4B), as described above with respect to sleeve 301.

Referring now to FIG. 10B, once the insertable sleeve 1401 is inserted and positioned onto the insertion portion 211, the user may break the perforated edge 1426 by, e.g., pulling the pull tab 1422, thereby forming a perforated pocket 1426. The user may then tuck the perforated pocket 1426 over a top edge of the top bill 203, as shown in FIG. 5D, to secure the insertable sleeve 1401 onto the speculum 200. In other embodiments, the perforated edge 1424 may be located elsewhere on the insertable sleeve 1401 (i.e., not on the petal 1420a). Alternatively, instead of a perforated edge 1426 used to create a perforated pocket 1426, the insertable sleeve 1401 may include a pocket preformed into the petal 1420a (e.g., the petal 1420a may include a flap of material formed in the shape of a pocket) or elsewhere on the sleeve 1401, such that the user may tuck the preformed pocket over the top edge of the top bill 203 to secure the sleeve 1401 onto the speculum 200. In still other embodiments, the sleeve 1401 may include another means of securing the insertable sleeve 1401 to the speculum 200, such as straps to wrap or fasten around a back of the speculum 200, an adhesive strip on the petal 1420a and/or the petal 1420b that sticks to the upper bill 203 and/or the lower bill 205, and so on.

Once a speculum is inserted into an insertable sleeve accessory positioned within the vagina of a patient, the speculum may be used to carry out a medical procedure on a patient. The medical procedure may be any gynecological examination or procedure, such an examination of the vaginal cavity, a pelvic examination, a Pap smear, an insertion or removal of an IUD, an insemination, an STI testing, a tissue collection, a biopsy, or an electrosurgery. To perform a procedure with a speculum, the user must move the speculum to the open position, as shown in FIG. 11, thereby expanding the insertable sleeve accessory, shown in FIG. 11 as insertable sleeve 1501. Insertable sleeve 1501 is configured, for example, similarly to insertable sleeve 301. The user then manipulates the lever 209 to separate and open the bills 203 and 205 and expand the sleeve 1501. The bills 203 and 205 open, for example, when a force is applied to the lever 209. When force is applied to the lever 209, the opening between the bills 203 and 205 created by the separation of the bills 203 and 205 may be caused by both bills 203 and 205 moving, or either bill 203 or bill 205 moving. For example, the force applied on the lever 209 may cause bill 203 to move, while bill 205 remains stationary. Bill 203 and/or bill 205 may be coupled to the upper portion of handle 207 by a hinge such that a force on lever 209 causes a rotational movement of bill 203 and/or bill 205 about the hinge, separating the ends of bills 203 and 205. In one embodiment of the speculum 200, the user may need to apply the force throughout the procedure in order to keep the bills 203 and 205 in the open position. In another embodiment of the speculum 200, the speculum 200 may contain a locking mechanism whereby the user may lock the bills 203 and 205 into the open position.

When a force is applied to the lever 209 and the bills 203 and 205 of the speculum 200 separate, the sleeve 1501 expands from a first state to a second state (i.e., from an unexpanded state to an expanded state). When the bills 203 and 205 separate, the sleeve 1501 may stretch to accommodate the increase in distance between bills 203 and 205. Beneficially, the expansion of the sleeve 1501 provides side wall retention for, e.g., obese women with extra tissue in the side walls of the vagina, allowing the user to maintain an uninterrupted view of the vaginal cavity and cervix while viewing the vaginal cavity and cervix through the speculum 200. The expansion of the sleeve 1501 also works to prevent vaginal tissue or pubic hair from entering the opening between the bills 203 and 205, as the bills 203 and 205 may cause pinching of the tissue or pubic hair that is painful for the patient when the bills 203 and 205 are returned to the closed position at the conclusion of the procedure, examination, or surgery.

Once the user has completed the procedure (e.g., inspection of the vaginal cavity and cervix, a Pap smear, an electrosurgery, etc.), the bills 203 and 205 should be returned to the closed position to remove the speculum 200 from the patient. To return the bills 203 and 205 to the closed position, the user may release the force from the lever 209. Removing the force, by itself, works to close the bills 203 and 205 for configurations of the speculum 200 where force needs to be applied to the lever 209 for the length of the procedure to maintain the viewing opening. However, for configurations of the speculum 200 where the lever 209 locks into place when the force is applied, a second force may also need to be applied to the lever 209 to overcome the locking mechanism and close the bills 203 and 205. The force may be applied in a direction opposite of the opening force. Alternatively, the lever 209 may be released by applying a second force in the same direction as the opening force to the lever 209 to move the lever 209 past the locking position, thereby releasing the lock and closing the bills 203 and 205. In configurations utilizing a toggle switch, the bills can be unlocked and closed by pressing the appropriate portion of the toggle switch. By returning the bills 203 and 205 to the closed position, the sleeve (e.g., sleeve 301, 401, 601, or 701) returns from the second position to the first position (i.e., from the expanded state to the unexpanded state).

Once the bills 203 and 205 of the speculum 200 are closed, the speculum 200 carrying the insertable sleeve accessory, such as insertable sleeve 301, 401, 501, 701a-c, 801, 901a-b, 1001a-b, 1101, 1201, 1301, 1401, and 1501, can be removed from the patient. The speculum 200 may then be pulled along an axis parallel to the length of bills 203 and 205 to easily remove the speculum 200 from the patient.

The insertable sleeve accessory may be removed from the insertion portion 211 of the speculum 200 after use. For example, the insertable sleeve may be peeled from the proximal end of the bills 203 and 205 to remove the insertable sleeve from the insertion portion 211. In some embodiments, the insertable sleeve may be removed by using a removal device that aids the user in sliding the sleeve off of the insertion portion 211. After removal, the insertable sleeve, if designed to be disposable, can be thrown away. In this way, the device remains relatively free of direct contact with the patient tissue by way of the insertable sleeve, and while sterilization procedures are still utilized, the speculum has a somewhat reduced risk of cross-contamination. The speculum may remain relatively clean during a medical procedure, examination, or surgery and can undergo a quicker and less intensive sterilization because the tissue-contacting sleeve is discarded after use and the device otherwise remains relatively free of contact with the patient tissue. Alternatively, the sleeve may be able to be sterilized for reuse. Sterilizing the sleeve may be more efficient and effective than sterilization of an unprotected speculum 200 after each use.

Figure 12:
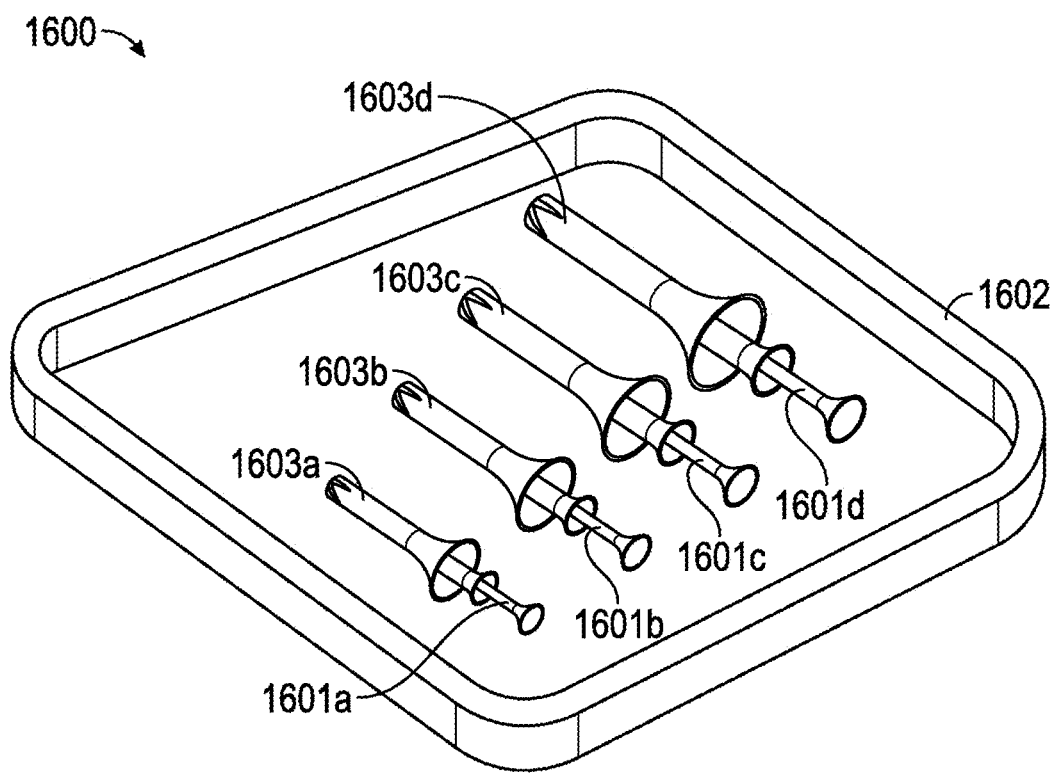
FIG. 12 depicts a kit of applicators carrying insertable modifier sleeves, according to an embodiment.

FIG. 12 depicts a kit 1600 according to an embodiment. As shown, a plurality of applicators 1603 and insertable sleeves 1601 may be provided in a kit. The applicators may come in a variety of sizes which can be selected for comfort by the patient or a practitioner. The applicators 1603a, 1603b, 1603c, and 1603d may be different sizes but contain an insertable sleeve 1601 of the same size, or the sleeves 1601a, 1601b, 1601c, and 1601d may also vary in size, corresponding with the size of the applicators 1601. The kit 1600 may come in a container 1602 such as a box, tray, or cartridge which holds the sleeves and the applicators. Each kit 1600 may be packaged individually, or a practitioner's office may be provided with a plurality of applicators 1603 and sleeves 1601 of each size and can create a kit to be presented to the patient for insertion. In other embodiments, the kit 1600 may additionally include one or more speculums 200. In one embodiment, the kit may include a plurality of speculums 200 of varying lengths and widths and of varying expansion capabilities (i.e., capable of opening the bills 203 and 205 in different ways, to different opening lengths, etc.) and one or more sleeves 1601 and applicators 1603 configured to fit the plurality of speculums 200. In another embodiment, the kit may include a plurality of sleeves 1601 and applicators 1603 of varying lengths and widths and one or more speculums 200. In yet another embodiment, the kit may further include accessories related to the needs of the examination or the procedure, for example, an IUD insertion device, a disposable electrosurgery tool, etc. In yet another embodiment, a plurality of sleeve accessories can be provided loosely in a large package or box.

The insertable sleeve accessory, such as insertable sleeve 301, 401, 501, 701a-c, 801, 901a-b, 1001a-b, 1101, 1201, 1301, 1401, and 1501, overcomes the previously described shortcomings of the traditional speculum in a variety of ways. First, the sleeve may be made of a rubber or other soft material that is warmer than the traditional metal speculum bills. As such, inserting a speculum with a sleeve accessory attached may be less shocking, and thus more comfortable, to a patient than a bare metal speculum. The material may be at least substantially transparent to allow for good visualization of the vaginal cavity through the speculum with attached sleeve. Furthermore, a slimmer profile speculum can be utilized because of the sleeve (e.g., because the sleeve allows for improved visualization such that a larger speculum is not necessary), which provides better comfort for the patient during the procedure, examination, or surgery involving the speculum. The sleeve moreover allows the speculum to be removed in a closed position while preventing the pinching of either tissues or pubic hair during the process, significantly improving patient comfort while reducing patient anxiety. Importantly, the sleeve also provides the side wall support between the upper bill and the lower bill of the speculum that allows the practitioner better and less impeded visualization into the vagina and cervix. When used during an electrosurgery, the sleeve accessory may additionally provide insulation to protect the vaginal walls of a patient during the electrosurgery procedure. Finally, the insertable sleeve allows the patient to be more actively involved in the procedure and provides the patient with the opportunity to perform the initial penetration into the body, reducing patient anxiety related to use of the speculum.

The foregoing description details certain embodiments of the systems, devices, and methods disclosed herein. It will be appreciated, however, that no matter how detailed the foregoing appears in text, the devices and methods can be practiced in many ways. As is also stated above, it should be noted that the use of particular terminology when describing certain features or aspects of the technology should not be taken to imply that the terminology is being re-defined herein to be restricted to including any specific characteristics of the features or aspects of the technology with which that terminology is associated. The scope of the disclosure should therefore be construed in accordance with the appended claims and any equivalents thereof.

It will be appreciated by those skilled in the art that various modifications and changes may be made without departing from the scope of the described technology. Such modifications and changes are intended to fall within the scope of the embodiments, as defined by the appended claims. It will also be appreciated by those of skill in the art that parts included in one embodiment are interchangeable with other embodiments; one or more parts from a depicted embodiment can be included with other depicted embodiments in any combination. For example, any of the various components described herein and/or depicted in the Figures may be combined, interchanged or excluded from other embodiments.

The devices, components, methods and systems described herein can be combined with one or more of the devices, components, methods and systems described in any of U.S. patent application entitled "Speculum with Secondary Bills," filed on Dec. 28, 2016 and identified by U.S. patent application entitled "Sleeve for Speculum and Use Thereof," filed on Dec. 28, 2016, and U.S. patent application entitled "Ergonomically Designed Vaginal Speculum," filed on Dec. 28, 2016, each of which is incorporated herein by reference in its entirety.

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims are generally intended as "open" terms (e.g., the term "including" should be interpreted as "including but not limited to," the terms "comprising" and "having" should, respectively, be interpreted as "comprising at least" and "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an." In general, "a" and/or "an" should be interpreted to mean "at least one" or "one or more"; the same holds true for the use of definite articles used to introduce claim recitations.

Furthermore, in those instances where a convention analogous to "at least one of A, B, and C, etc." is used, in general, such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general, such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The technology disclosed herein has numerous applications and while particular embodiments of the technology have been described in detail, it will be apparent to those skilled in the art that the disclosed embodiments may be modified given the design considerations discussed herein. Therefore, the foregoing description is to be considered exemplary rather than limiting, and the true scope of the invention is that defined in the following claims.

What is claimed is:

1. A device for use with a medical speculum, comprising:
an insertable sleeve comprising a sleeve body, the sleeve body comprising:
an outer surface; and
an inner surface defining a hollow sleeve channel having a proximal end and a distal end, the proximal end having an opening, wherein the sleeve body is configured to be inserted into a vaginal cavity of a patient, wherein the sleeve body is configured to receive an insertion portion of the medical speculum in the hollow sleeve channel subsequent to being inserted into the vaginal cavity, wherein the insertion portion of the medical speculum comprises an upper bill and a lower bill, and wherein the sleeve body is configured to expand and conform to the upper bill and the lower bill as a space between the upper bill and the lower bill is increased from a closed position to an open position of the medical speculum,
wherein the proximal end of the sleeve body comprises a gradual broadening of the sleeve body, the gradual broadening of the sleeve body extending beyond the insertion portion of the medical speculum, the gradual broadening of the sleeve body integrally formed with the sleeve body and wherein a portion of the sleeve body has a uniform diameter;
an applicator configured to facilitate insertion and positioning of the sleeve body into the vaginal cavity, the applicator comprising:
a tube configured to carry the sleeve body; and
a plunger extending from the tube, a length of the plunger aligned with a length of the tube, the applicator configured to release the sleeve body from the tube into the vaginal cavity in response to a user depressing the plunger into the tube, wherein a portion of the released sleeve body is adapted for insertion into the vaginal cavity.

2. The device of claim 1, wherein the uniform diameter of the sleeve body is between 0.25 inches and 4.0 inches.

3. The device of claim 1, wherein the sleeve body and/or the applicator is disposable.

4. The device of claim 1, wherein the sleeve body comprises one or more of the following to assist with adherence of the sleeve to the insertion portion: gripping elements positioned on the inner surface of the sleeve body, ribbed details, and a texture difference on the inner surface.

5. The device of claim 1, wherein the sleeve body comprises one or more of the following: folds, fluting, webbing, and ribs, thereby providing structure to the sleeve body to help during insertion.

6. The device of claim 1, wherein the sleeve body further comprises an internal tab extending along a length of the inner surface of the sleeve body from the distal end to outside of the opening of the proximal end, the tab configured to add stiffness to the sleeve body, and wherein a portion of the tab extending outside of the opening of the proximal end is configured to be held by the user while inserting the insertion portion of the medical speculum into the sleeve body.

7. The device of claim 1, further comprising a flap configured to secure the insertable sleeve to the medical speculum by tucking the flap over a top edge of the medical speculum.

8. The insertable sleeve of claim 7, wherein the sleeve body comprises one or more of the following to assist with adherence of the sleeve to the insertion portion: gripping elements positioned on the inner surface of the sleeve body, ribbed details, and a texture difference on the inner surface.

9. The device of claim 1, wherein the sleeve body is made of a rubber or a plastic material.

10. The device of claim 9, wherein the rubber or plastic material is one of a polyisoprene, a polyurethane, a thermoplastic polyurethane, a styrene copolymer, and a thermoplastic elastomer.

11. The device of claim 1, wherein the sleeve body is coated with at least one of a lubricant, a powder, a surface texture, a bioactive agent, and a therapeutic agent.

12. The device of claim 1, wherein the proximal end is edged with a ridged finish.

13. The device of claim 1, wherein the sleeve body is made of a transparent material to allow visibility through the sleeve body.

14. The device of claim 1, comprising a closed distal end, wherein the closed distal end further comprises an aperture.

15. The device of claim 1, wherein the applicator is made of a rubber, plastic, or cardboard material.

16. The device of claim 1, wherein the applicator comprises a gripping element to facilitate grasping of the applicator during insertion of the sleeve body into the vaginal cavity.

17. The device of claim 1, wherein the device is packaged in a single-product package.

18. A kit comprising:
a speculum comprising a handle and an insertion portion, the insertion portion comprising an upper bill and a lower bill coupled to the handle; and
the device of claim 1.

19. The kit of claim 18, further comprising a plurality of speculums, varying in length, width, and expansion capabilities.

20. An insertable sleeve for use with a medical speculum, comprising:
a sleeve body, comprising:
an outer surface;
an inner surface defining a hollow sleeve channel having a proximal end and a distal end, the proximal end having an opening; and
a tab extending along a length of the inner surface of the sleeve body from the distal end to outside of the opening of the proximal end, the tab configured to add stiffness to the sleeve body, wherein the sleeve body is configured to be inserted into a vaginal cavity of a patient without an applicator, wherein the sleeve body is configured to receive an insertion portion of the medical speculum in the hollow sleeve channel subsequent to being inserted into the vaginal cavity, and wherein a portion of the tab extending outside of the opening of the proximal end is configured to be held by a user while inserting the insertion portion of the medical speculum into the sleeve body, the sleeve body configured to expand and conform to an upper bill and a lower bill of the medical speculum as a space between the upper bill and the lower bill is increased from a closed position to an open position,
wherein the proximal end of the sleeve body comprises a gradual broadening of the sleeve body, and wherein a portion of the sleeve body has a uniform diameter from the distal end to the proximal end.

* * * * *